United States Patent
Cho et al.

(10) Patent No.: US 10,344,260 B2
(45) Date of Patent: Jul. 9, 2019

(54) MELANOCYTE OR PROGENITOR CELL THEREOF ADAPTED TO KERATINOCYTE, AND PREPARATION METHOD THEREOF

(71) Applicant: AMOREPACIFIC CORPORATION, Seoul (KR)

(72) Inventors: Eun Gyung Cho, Yongin-si (KR); Bum Ho Bin, Yongin-si (KR); Tae Ryong Lee, Yongin-si (KR); Ji Yeon Han, Yongin-si (KR); Hyun Jung Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 82 days.

(21) Appl. No.: 14/346,995

(22) PCT Filed: Sep. 27, 2012

(86) PCT No.: PCT/KR2012/007815
§ 371 (c)(1),
(2) Date: Mar. 25, 2014

(87) PCT Pub. No.: WO2013/048139
PCT Pub. Date: Apr. 4, 2013

(65) Prior Publication Data
US 2014/0227779 A1    Aug. 14, 2014

(30) Foreign Application Priority Data

Sep. 30, 2011  (KR) .................. 10-2011-0099728
Aug. 27, 2012  (KR) .................. 10-2012-0093805

(51) Int. Cl.
*C12N 5/071*  (2010.01)

(52) U.S. Cl.
CPC ........ *C12N 5/0626* (2013.01); *C12N 2500/14* (2013.01); *C12N 2506/094* (2013.01)

(58) Field of Classification Search
None
See application file for complete search history.

(56) References Cited

U.S. PATENT DOCUMENTS

| 4,757,019 A | 7/1988 | Eisinger et al. |
| 5,712,163 A | 1/1998 | Parenteau et al. |
| 6,126,935 A * | 10/2000 | Van Bossuyt .......... A61K 35/36 424/520 |

FOREIGN PATENT DOCUMENTS

| CA | 1 233 135 A | 2/1988 |
| CN | 101892286 A | 11/2010 |
| JP | 61-56130 A | 3/1986 |
| KR | 10-0981088 B1 | 9/2010 |
| KR | 10-2011-0087473 A | 8/2011 |
| WO | WO 2010/039681 A1 | 4/2010 |

OTHER PUBLICATIONS

Carsberg et al., Ultraviolet radiation-induced melanogenesis in human melanocytes, Effects of modulating protein kinase-C, Journal of Cell Science vol. 107, pp. 2591-2597 (1994).*
Aasen et al., Isolation and cultivation of human keratiocytes from skin or plucked hair for the generation of induced pluripotent stem cells, Nature Protocols, vol. 5, No. 2, pp. 371-382, 2010.*
Medium 254, ThermoFisher Technical Resources, retrieved from the internet, Oct. 26, 2015: www.thermofisher.com/us/en/home/technical-resources/media-formulation.281.html.*
Ohta et al., Generation of Human Melanocytes from Induced Pluripotent Stem Cells, PloS One (6) 1: e16182, pp. 1-10, 2011.*
Swope et al., Long-term Proliferation of Human Melanocytes Is Supported by the Physiologic Mitogens alpha-Melanotropin, Endothelin-1, and Basic Fibroblast Growth Factor, Experimental Cell Research, vol. 217, pp. 453-459, 1995.*
Xie et al., Calcium-induced Human Keratinocyte Differentiation Requies src- and fyn-mediated Phosphatidylinositol 3-Kinase-dependent Activation of Phospholipase C-gamma 1, Molecular Biology of the Cell, vol. 16, pp. 3236-3246, Jul. 2005.*
UCSF Media Production Formulations, MEM EBSS, Apr. 11, 2007, retrieved from the internet: www.ccf.ucsf.edu/protocols/ccfac001.pdf.*
Bamberger et al., Retinoic acid inhibits downregulation of DeltaNp63alpha expression during terminal differentiation of human primary keratinocytes, The Journal of Investigative Dermatology, vol. 118, No. 1, 2002, pp. 133-138.*
Beck et al., Tissue Engineering, vol. 9, No. 6, 2003, pp. 1123-1131.*
Lonza, Clonetics keratinocyte cell systems, NHEK & D-HEK, Technical Sheet, pp. 1-2 (2011), retrieved from the internet: www.lonza.com.*
Media: Ham's F-10 medium product brochure, retrieved from the internet Jun. 16, 2017: http://www.biochrom.de/fileadmin/user_upload/service/produktinformation/englisch/BC_catalogue_46_F10.pdf.*
Lonza, Clonetics keratinocyte media products brochure, retrieved from the internet:http://bio.lonza.com/uploads/tx_mwaxmarketingmaterial/Lonza_ManualsProductInstructions_Clonetics_Keratinocyte_Media_Products.pdf.*
Office Action dated Feb. 28, 2015 for Chinese Patent Application No. 201280048174.4.

(Continued)

*Primary Examiner* — Thomas J. Visone
*Assistant Examiner* — Evelyn Y Pyla
(74) *Attorney, Agent, or Firm* — Merchant & Gould P.C.

(57) ABSTRACT

The present invention relates to novel melanocytes and melanoblasts. In addition, the present invention relates to a novel method for producing melanocytes and melanoblasts. Specifically, provided is novel melanocytes of which gene expression, melanin content, and tyrosinase activity are different from those of conventional melanocytes. Even more specifically, provided is novel melanoblasts of which the gene expression, the melanin content the tyrosinase activity, and the protein expression are different from those of conventional melanocytes. Additionally, provided is a novel method for producing melanocytes or melanoblasts by culturing keratinocytes.

13 Claims, 13 Drawing Sheets

(56) References Cited

OTHER PUBLICATIONS

Extended European Search Report dated Feb. 5, 2015 for European Patent Application No. 12834846.3.
Cook et al., "Human Melanoblasts in Culture: Expression of BRN2 and Synergistic Regulation by Fibroblast Growth Factor-2, Stem Cell Factor, and Endothelin-3", *Journal of Investigative Dermatology*, 121(5):1150-59 (Nov. 1, 2003), XP055165044, ISSN: 0022-202X.
Hirobe et al., "Keratinocytes Are Involved in Regulating the Developmental Changes in the Proliferative Activity of Mouse Epidermal Melanoblasts in Serum-Free Culture", Developmental Biology, Academic Press, Amsterdam, NL, vol. 161, No. 1, (Jan. 1, 1994), pp. 59-69, XP024779790, ISSN: 0012-1606.
Hirobe T., "Melanocyte Stimulating Hormone Induces the Differentiation of Mouse Epidermal Melanocytes in Serum-Free Culture", *Journal of Cellular Physiology*, 152(2):337-45 (Aug. 1, 1992), XP009025292, ISSN: 0021-9541.
Cho et al., "Novel Method for Isolating Human Melanoblasts from Keratinocyte Culture", *Pigment Cell & Melanoma Research*, 27(3):489-94 (May 24, 2014), XP055165039, ISSN: 1755-1471.
De Luca et al., "Human Epithelial Cells Induce Human Melanocyte Growth In Vitro but Only Skin Keratinocytes Regulate Its Proper Differentiation in the Absence of Dermis," *The Journal of Cell Biology*, 107:1919-26 (1988).
International Search Report for International Patent Application No. PCT/KR2012/007815 (dated Dec. 14, 2012).
Office Action dated Aug. 30, 2016 for Japanese Patent Application No. 2014-533201.
Hirobe, "Endothelins are Involved in Regulating the Proliferation and Differentiation of Mouse Epidermal Melanocytes in Serum-Free Primary Culture," *Journal of Investigative Dermatology Symposium Proceedings*, 6(1):25-31 (2001).
Notice of Allowance from Korean Appl'n. No. 10-2012-0093805, dated Oct. 30, 2018.
De Luca et al., "Human Epithelial Cells Induce Human Melanocyte Growth in Vitro but Only Skin Keratinocytes Regulate it's Proper Differentiation in the Absence of Dermis," The Journal of Cell Biology, vol. 107, Nov. 1, 1988, pp. 1919-1926.

\* cited by examiner

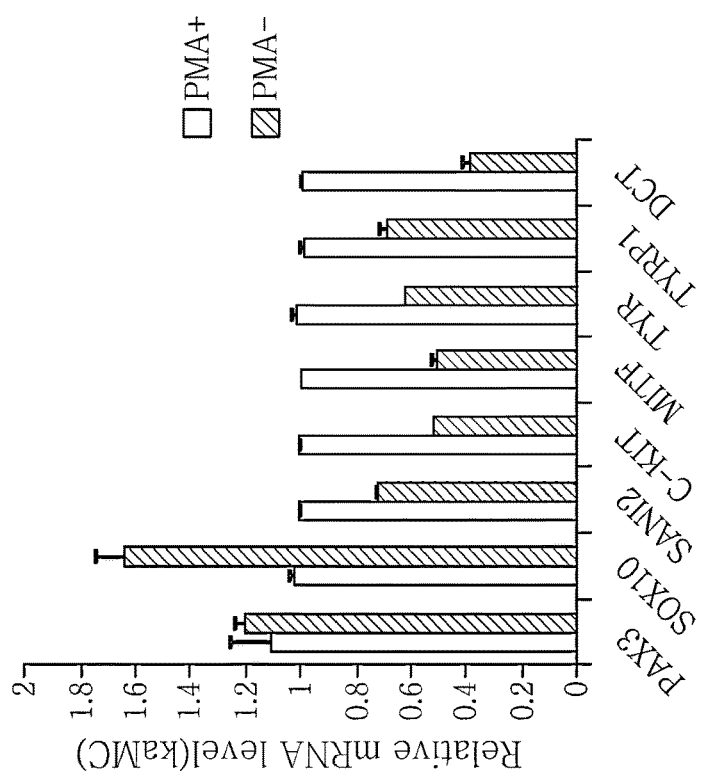
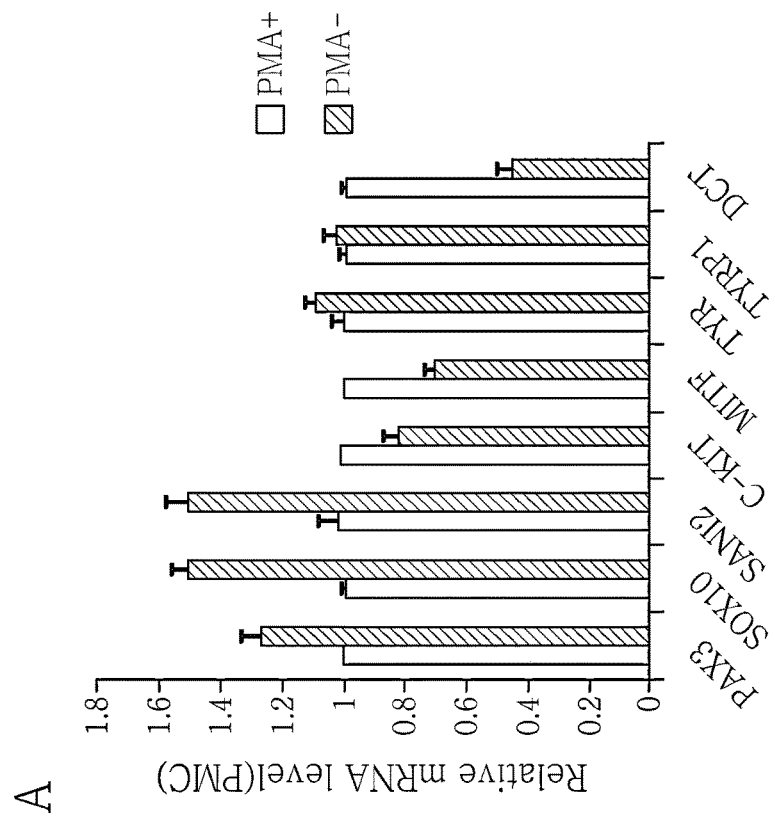
Fig.6

Fig. 8
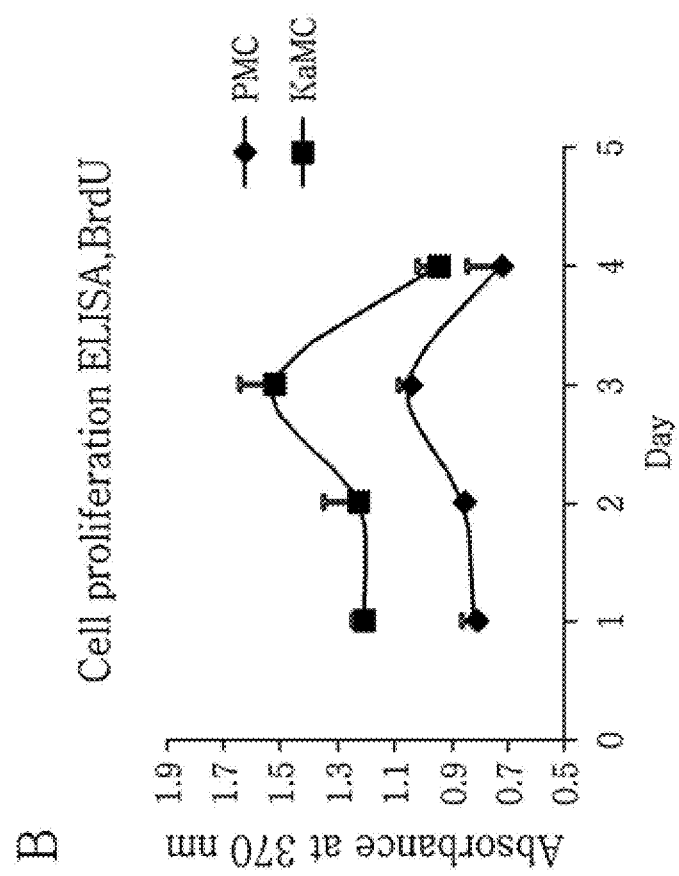
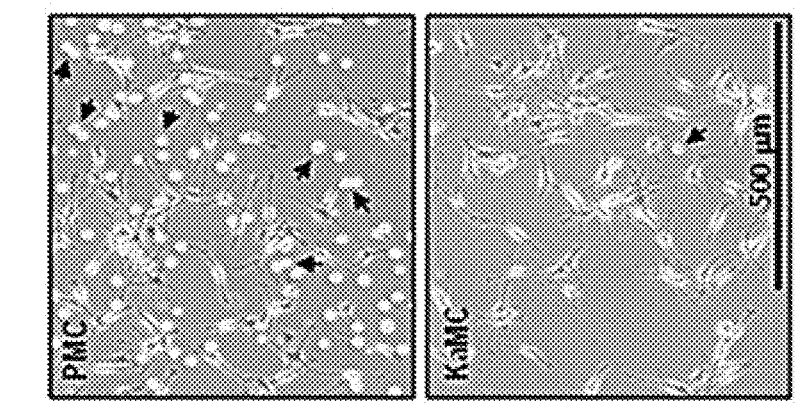

Fig.12
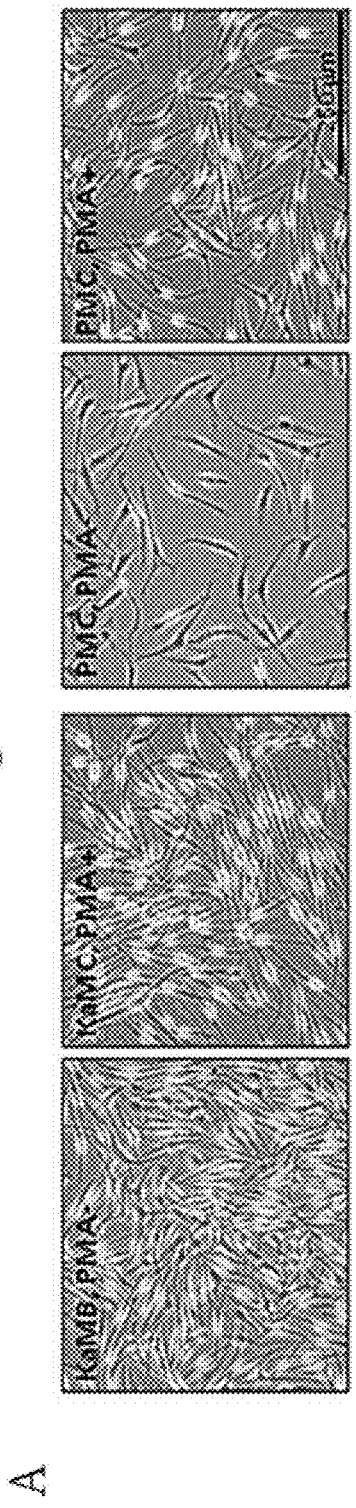
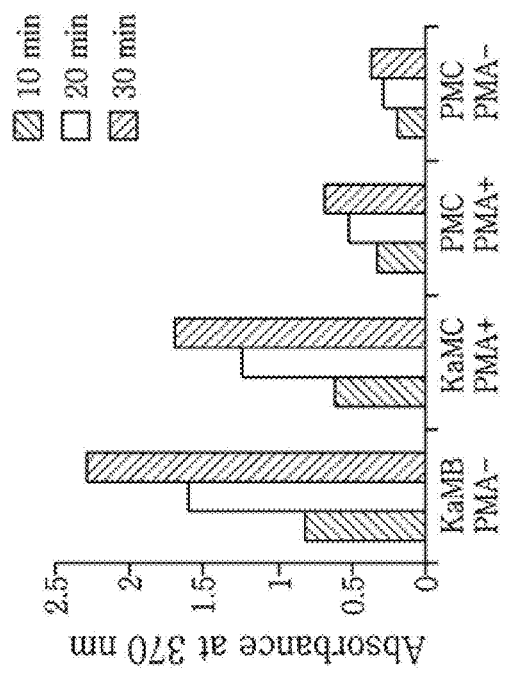
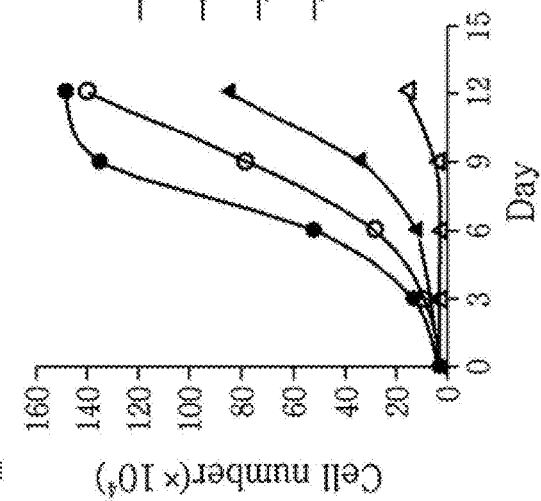

MELANOCYTE OR PROGENITOR CELL THEREOF ADAPTED TO KERATINOCYTE, AND PREPARATION METHOD THEREOF

This application is a U.S. National Stage Application under 35 U.S.C. § 371 of International Patent Application No. PCT/KR2012/007815 filed 27 Sep. 2012, which claims the benefit of priority to Korean Patent Application No. 10-2011-0099728 filed 30 Sep. 2011 and Korean Patent Application No. 10-2012-0093805 filed 27 Aug. 2012, the disclosures of all of which are hereby incorporated by reference in their entireties. The International Application was published in Korean on 4 Apr. 2013 as WO 2013/048139.

TECHNICAL FIELD

The present disclosure relates to melanocytes or melanoblasts as progenitor cells thereof, which are adapted to keratinocytes. Further, the present disclosure relates to a method for producing the melanocytes or melanoblasts as progenitor cells thereof, which are adapted to keratinocytes.

BACKGROUND ART

The number of melanocytes in epidermis is very few as much as 1/10 of the number of keratinocytes. According to conventional separation methods, melanocytes are separated by: additionally treating an epidermal sheet, which is obtained by treating the skin tissue with dispase, with an enzyme such as trypsin to make single cells, and then providing a medium containing specific growth factors or chemokines to the cells to make only melanocytes survive. In respects that the melanocytes exist very few and there is no specific separation method except a medium, directly separating melanocytes from a living body is inefficient. For this reason, the price of commercial melanocytes is relatively expensive, compared with that of keratinocytes.

On the other hand, the melanocytes separated from a living body have limited homogeneity and proliferation capacity. Further, when using melanocytes in vitro shortly after directly separating the melanocytes from the epidermal sheet, it was reported that the cells have no response to stimulation such as UVB, or rather the expression of the genes related to melanin synthesis was reduced. In order to solve the above problems, measures, for example, treating UVB to co-culture of keratinocytes and melanocytes, or treating UVB to single-culture of keratinocytes followed by providing the culture to melanocytes, were needed.

It is needed to develop a method for separating melanocytes: which overcome the above shortcomings of the conventionally separated melanocytes, and thereby, having good homogeneity and proliferation capacity, and whose function can be studied without co-culturing them because their characteristics in vitro are maintained similar with the characteristics of when they are present in the body.

On the other hand, it is known that melanocytes are terminally differentiated from melanocyte stem cells, which are derived from neural crest during a developmental process, and melanoblasts as progenitor cells. The melanoblasts have better proliferation capacity and differentiation capacity than melanocytes, and have cell mobility (migration) as a characteristic of a developmental process.

Studies about development and differentiation from neural crest stem cell-melanoblast to melanocyte, and functions of the genes related to the above process have been done a lot in a mouse, but as a result of trial to separate melanoblasts by using some differentiation initial markers, yield was less than 5%. Furthermore, because the epidermal structure of the mouse is different from that of human, and there is no specific marker for dividing each differentiation steps, reports about methods for identifying the presence of melanoblasts in the human adult epidermis, or for directly separating melanoblasts from the skin tissue and culturing them are very rare. Some methods for inducing melanoblastic characters by changing a medium of the already separated melanocytes were reported, but it is hard to say that the cells are the melanoblasts existing in the human skin.

DISCLOSURE

Technical Problem

The present disclosure is directed to providing a melanocyte, which has good proliferation capacity resulting from its good homogeneity, engraftment capacity and viability.

The present disclosure is also directed to providing a melanocyte having melanin forming capacity.

The present disclosure is also directed to providing a melanocyte, which may be studied alone, without measures such as treating UVB to co-culture of a keratinocyte and a melanocyte, or treating UVB to single-culture of a keratinocyte followed by providing the culture to a melanocyte.

The present disclosure is also directed to providing a melanocyte, which is adapted to a keratinocyte in vitro in a state of maintaining relationship with the keratinocyte.

The present disclosure is also directed to providing a separated human melanoblast and a method for producing thereof.

The present disclosure is also directed to providing a human melanoblast adapted to a keratinocyte and a method for producing thereof.

Technical Solution

In one aspect, there is provided a method for producing melanocytes or melanoblasts as progenitor cells thereof adapted to a keratinocyte, which includes: (a) culturing keratinocytes in a keratinocyte medium in a dish; (b) removing the keratinocytes from the culture; and (c) collecting cells attached to the bottom of the dish from the culture, in which the keratinocyte is removed, and culturing the collected cells in a melanocyte medium or a melanoblast medium.

The method according to one aspect of the present disclosure may be a method for producing melanocytes, and the melanocyte medium may be a basal medium supplemented with supplements, wherein the basal medium comprises essential and non-essential amino acids, vitamins, organic compounds, trace minerals and inorganic salts, but do not comprise antibiotics, antimycotics, hormones, growth factors or proteins, wherein the supplements comprise fetal bovine serum, basic fibroblast growth factor, bovine pituitary extract, heparin, hydrocortisone, insulin, transferrin and phorbol 12-myristate 13-acetate (PMA). The supplement may further include Dimethyl sulfoxide (DMSO).

The method according to one aspect of the present disclosure may be a method for producing melanoblasts, and the melanoblast medium may be basal medium supplemented with supplements, wherein the basal medium comprises essential and non-essential amino acids, vitamins, organic compounds, trace minerals and inorganic salts, but do not comprise antibiotics, antimycotics, hormones, growth factors or proteins, wherein the supplements comprise fetal bovine serum, basic fibroblast growth factor, bovine pituitary extract, heparin, hydrocortisone, insulin, transferrin and endothelin-1.

The melanocytes adapted to a keratinocyte according to one aspect of the present disclosure may be melanocytes adapted to a keratinocyte, which has at least one characteristic selected from the following characteristics: (i) an expression level of p75NTR, which is a neural crest stem cell marker lower than a primary melanocyte; (ii) an expression level of BRN2, which is expressed in a melanoblast higher than a primary melanocyte; (iii) a melanin content higher than a primary melanocyte; (iv) a tyrosinase activity higher than a primary melanocyte; (v) an increased expression level of p75NTR higher than a primary melanocyte when cultured in a phorbol 12-myristate 13-acetate (PMA)-free medium; (vi) an increased expression level of BRN2 lower than a primary melanocyte when cultured in a PMA-free medium; (vii) a characteristic that a relative ratio of the p75NTR expression level of the melanocyte adapted to a keratinocyte cultured in a PMA-free medium, to the p75NTR expression level of the melanocyte adapted to a keratinocyte cultured in a PMA-containing melanocyte medium, is equivalent to about 60 to about 160% of the ratio of the p75NTR expression level of the primary melanocyte cultured in a PMA-containing melanocyte medium, to the p75NTR expression level of the melanocyte adapted to a keratinocyte cultured in a PMA-containing melanocyte medium; (viii) a characteristic that a relative ratio of the BRN2 expression level of the melanocyte adapted to a keratinocyte cultured in a PMA-free medium, to the BRN2 expression level of the melanocyte adapted to a keratinocyte cultured in a PMA-containing melanocyte medium, is equivalent to about 1 to about 10 times of the ratio of the BRN2 expression level of the melanocyte adapted to a keratinocyte cultured in a PMA-containing melanocyte medium, to the BRN2 expression level of the primary melanocyte cultured in a PMA-containing melanocyte medium; and (ix) a ratio of the cell attached to the bottom of a dish after 2 hour subculture higher than a primary melanocyte.

The melanoblast according to one aspect of the present disclosure may be a melanoblast adapted to a keratinocyte, which has a characteristic that the expression level of at least one melanoblast marker selected from the group consisting of MITF, DCT, TYRP1, SNAI2, C-KIT and EDNRB is higher than a primary melanocyte.

Advantageous Effects

From one aspect, the present disclosure may provide a melanocyte or a melanoblast having good proliferation capacity resulting from its excellent homogeneity, engraftment capacity and viability.

From one aspect, the present disclosure may provide a melanocyte having melanin forming capacity.

From one aspect, the present disclosure may provide a melanocyte, which may be studied alone, without measures such as treating UVB to co-culture of a keratinocyte and a melanocyte, or treating UVB to single-culture of a keratinocyte followed by providing the culture to a melanocyte.

From one aspect, the present disclosure may provide a melanocyte or a melanoblast adapted in vitro while keeping the relation with a keratinocyte.

From one aspect, the present disclosure may make sure feasibility of studies of a melanocyte or a melanoblast conducted in vitro.

From one aspect of the present disclosure, risk factors and treatment methods of skin hyperpigmentation such as nevi, lentigo and age spot, achromatosis such as vitiligo (leukoplakia and albinism) or canities, or cancer such as melanoma may be found through studies of survival, propagation, differentiation and regeneration of a melanocyte or a melanoblast.

From one aspect, the present disclosure may facilitate the development of whitening cosmetics and medicines, which have purposes on reducing melisma and freckles, and inhibiting melanin pigment formation.

DESCRIPTION OF DRAWINGS

The above and other aspects, features and advantages of the disclosed exemplary embodiments will be more apparent from the following detailed description taken in conjunction with the accompanying drawings in which:

FIG. 6 is graphs showing change on expression in PMC and KaMC depending on the presence of PMA, respectively (A, B);

FIG. 8 is images comparing initial engraftment capacities of PMC and KaMC (A) and cell proliferation capacities thereof (B);

FIG. 12 is images of each cell growing in a PMA− medium or a PMA+ medium (A), a graph showing cell number of each cell with time (B), and a graph comparing proliferation capacity of each cell by BrdU labeling (C) (Scale bar, 250 μm)

BEST MODE

Figure 1:
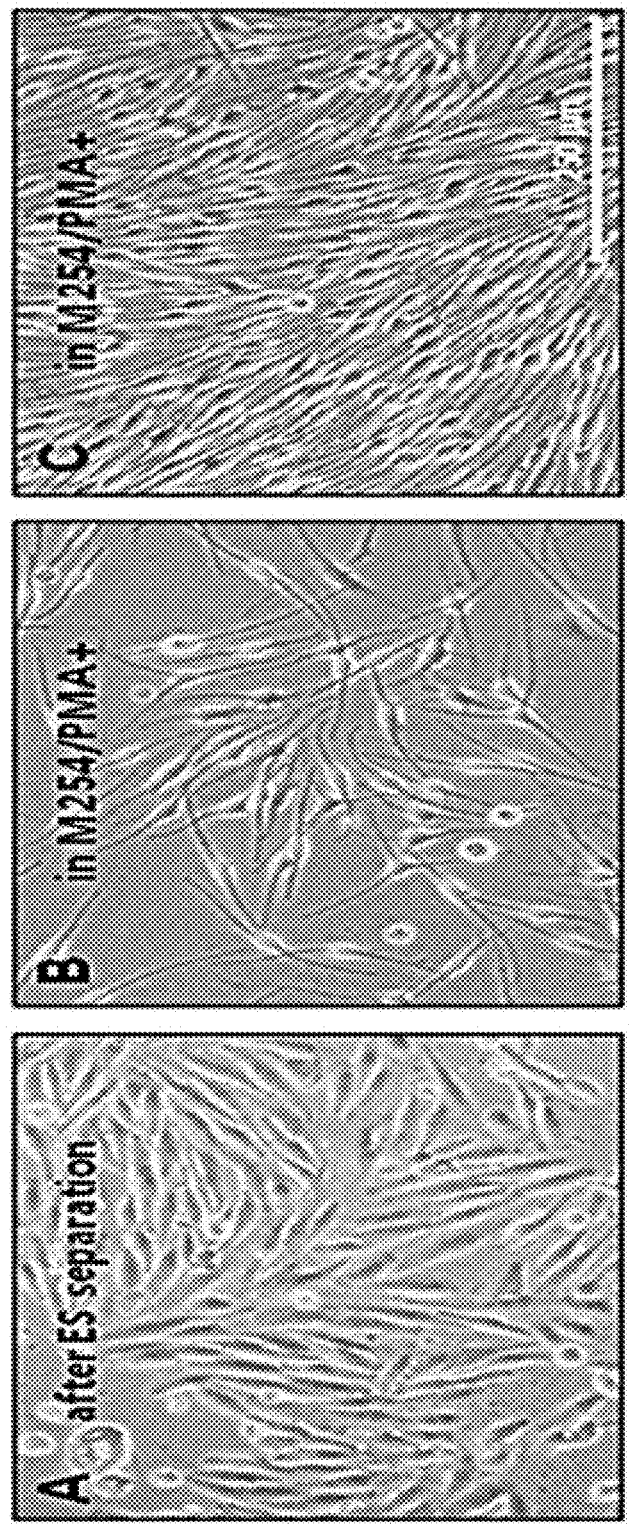
FIG. 1 is images showing cells remained at the bottom of a dish right after separating a cultured cell layer (A), the cells, which are remained at the bottom of a dish, growing in a melanocyte medium (B), and melanocytes growing with high density after subculturing the cells of (B) (C)

Hereinafter, the present disclosure is described in detail.

In this description, the term "primary melanocyte ("PMC")" refers to a melanocyte directly separated from a living body.

In this description, the term "melanoblast adapted to a keratinocyte (Keratinocyte-adapted Melanoblast, "KaMB")" refers to a melanoblast obtained by culturing a keratinocyte in vitro.

In this description, the term "a melanocyte adapted to a keratinocyte (Keratinocyte-adapted Melanocyte, "KaMC")" refers to a melanocyte, which is obtained by culturing a keratinocyte in vitro, and has a basic characteristic of a primary melanocyte but also at least one different characteristic.

The term "keratinocyte medium" used herein refers to a medium for culturing a human keratinocyte, and it may be any medium known in the art. For example, the keratinocyte medium may be a medium containing Bovine Pituitary Extract (BPE), human epidermal growth factor (hEGF), bovine Insulin, Hydrocortisone, and gentamicin and amphotericin-B (GA-1000). Further, it also may be a medium further containing epinephrine and transferrin in addition to the above ingredients. Examples of the medium, which may be commercially obtained, may be KGM™ (keratinocyte growth medium) (Cat. No. CC-3001; Lonza), KGM™ BULLETKIT™ (keratinocyte growth medium kit including supplements and growth factors in separate aliquots) (Cat. No. CC-3111; Lonza), KGM™ 2 BULLETKIT™ (keratinocyte growth medium kit including supplements and growth factors in separate aliquots) (Cat. No. CC-3107; Lonza) and KGM-GOLD™ BULLETKIT™ (keratinocyte growth medium kit including supplements and growth factors in separate aliquots) (Cat. No. 192060; Lonza).

The term "melanocyte medium" used herein refers to a medium for culturing a melanocyte, and it may be any medium known in the art. For example, it may be a melanin forming medium, which contains essential and non-essential amino acids, vitamins, organic compounds, trace mineral and inorganic salts, but does not contain antibiotics, antimycotics, hormone, growth factor or protein. Specifically, the melanocyte medium may be a medium supplemented with a supplement containing growth factor, hormone and tissue extract, which are essential for melanocyte growth, in order to plate human melanocyte and proliferate them for a long time. For example, the supplements may contain fetal bovine serum, basic fibroblast growth factor, bovine pituitary extract, heparin, hydrocortisone, insulin, transferrin and phorbol 12-myristate 13-acetate (PMA). The supplement may further include Dimethyl sulfoxide (DMSO)

The example of the supplement may be Human Melanocyte Growth Supplement (HMGS, cat. # S-002-5, Cascade Biologics). An example of a commercially available basic medium for a melanocyte supplemented with HMGS may be M254 medium (Cascade Biologics).

The term "melanoblast medium" used herein refers to a medium for culturing a melanoblast, and it may be any medium known in the art. For example, it may be a melanoblast medium, which contains essential and non-essential amino acids, vitamins, organic compounds, trace mineral and inorganic salts, but does not contain antibiotics, antimycotics, hormone, growth factor or protein. Specifically, the melanoblast medium may be a medium supplemented with a supplement containing growth factor, hormone and tissue extract, which are essential for melanoblast growth, in order to plate human melanoblast and proliferate them for a long time. For example, the supplement may contain fetal bovine serum, basic fibroblast growth factor, bovine pituitary extract, heparin, hydrocortisone, insulin, transferrin and endothelin-1.

The supplement may be PMA-Free Human Melanocyte Growth Supplement-2 (PMA-Free HMGS-2, cat. # S-016-5, Cascade Biologics). An example of a commercially available basal medium for a melanoblast supplemented with HMGS-2 may be M254 medium (Cascade Biologics).

The term "PMA-containing medium" used herein refers to a medium containing phorbol 12-myristate 13-acetate (PMA), which helps differentiation to a melanocyte.

The term "calcium medium" used herein refers to a keratinocyte medium added with calcium. For example, it may be a calcium medium, wherein $CaCl_2$ is added to a keratinocyte medium at the concentration of about 1.0 to about 1.6 mM, or about 1.2 to about 1.4 mM.

The term "phorbol 12-myristate 13-acetate (PMA)-free medium" used herein refers to a medium for culturing a human melanoblast, which does not contain PMA but contains endothelin-1. An example of a commercially available medium may be M254 medium supplemented with PMA-free HMGS-2 (Cascade Biologics, Cat. No.: S-016-5).

The term "p75NTR" used herein refers to a gene of low affinity neurotrophin receptor as a neural crest stem cell marker, which has ACCESSION No. NM_002507, VERSION: NM_002507.3, GI: 295842401.

The term "BRN2" used herein refers to mRNA of *Homo sapiens* POU class 3 homeobox 2 (POU3F2) as a gene expressed in a melanoblast. It is deposited as ACCESSION No. NM_005604, VERSION: NM_005604.2, GI: 51702520.

The term "EDNRB" used herein refers to a human endothelin receptor type B (NM_001122659.2) gene, and it is located on Chr. 13: 78469616-78492966.

The term "C-KIT" used herein refers to a human v-kit Hardy-Zuckerman 4 feline sarcoma viral oncogene homolog (NM_001093772.1) gene, and it is located on Chr. 4:55524095-55606881.

The term "SNAI2" used herein refers to a human snail homolog 2 (NM_003068.4), and it is located on Chr. 8: 49830236-49833988.

The term "MITF" used herein refers to a human microphthalmia-associated transcription factor (NM_198158.2), and it is located on Chr. 3: 69788586-70017488.

The term "DCT" used herein refers to a human dopachrome tautomerase, and it is located on Chr. 13: 95091835-95131936.

The term "TYRP1" used herein refers to a human tyrosinase-related protein 1 (NM_000550.2), and it is located on Chr. 9: 12693386-12710266.

The term "phorbol 12-myristate 13-acetate (PMA)" used herein refers to a material inducing melanocyte differentiation.

A melanocyte is a cell, which produces protective melanin pigment, has dendrites in terms of morphology and exists in the basal layer of epidermis at the ratio of about 1:4 to about 1:10 to basal cells. One melanocyte is contacting to 36 keratinocytes (pigmentation unit) making up a basal layer or a spinous layer through dendrites. Melanin has a function of protecting a nucleus of a keratinocyte from UV. Accordingly, it was known that people having small amount of melanin is likely to get skin cancer. There is no difference on the number of melanocytes between races, but the number and size of melanosome, the degree of melanization, the distribution of melanosome and the amount of melanin accumulated by degradation in a keratinocyte are different between races. Accordingly, skin color is determined by those factors. It was known that the number of tyrosinase, an enzyme important for melanin synthesis and the number of melanocytes are decreased as age increase. The melanocyte is the cell derived from a neural crest during a developmental process, and differentiates from a melanocyte stem cell and a melanoblast as a progenitor cell thereof to a melanocyte which synthesizes and releases melanin.

The method for producing melanocytes or melanoblasts as a progenitor cell thereof, which is adapted to a keratinocyte, according to one embodiment of the present disclosure, includes: (a) culturing keratinocytes in a keratinocyte medium in a dish; (b) removing the keratinocytes from the culture; and (c) collecting cells attached to the bottom of the dish from the culture, in which the keratinocyte is removed, and culturing the collected cells in a melanocyte medium or a melanoblast medium.

The keratinocyte of the step (a) may be a human keratinocyte.

The human keratinocyte may be any keratinocyte derived from human. A keratinocyte, which is directly separated from human or cultured after separation, and a keratinocyte derived from other cells also may be used. Examples of a commercially available human keratinocyte may be NHEK-Neo, Pooled (Neonatal Normal Human Epidermal Keratinocytes, Pooled: Cat. No. 00192906, Tissue acquisition No. P867, white people), NHEK-Neo (Cat. No. 00192907, Tissue acquisition No.: 20647, white people), NHEK-Adult (Cat. No. 00192627, Tissue acquisition No.: 21155, white people), NHEK-Neo (Cat. No. 00192907, Tissue acquisition No.: 18080, black people), provided from Lonza. In order to maintain a characteristic that a keratinocyte is attached to a base membrane and proliferates, a dish may be coated with about 0.1 to about 0.2% gelatin or about 1 to about 10 μg/ml collagen-type I, specifically. The cell may be cultured in an incubator of about 35 to about 37° C., about 5 to about 10% $CO_2$, and may be subcultured when reached to about 70 to about 80% density.

The step (b) may include: (i) culturing the cultured keratinocytes in a calcium medium, in which calcium is added to a keratinocyte medium; (ii) removing the calcium medium, washing the cell, exchanging the medium with a keratinocyte medium and culturing the cells again; (iii) removing the medium, washing the cell and then incubating the cell; and (iv) separating the keratinocyte in a sheet form by adding a buffer or a keratinocyte medium to the incubated cell.

The step (a) moves on the step (b) when the cell is cultured in a culture dish at about 80 to about 100% confluency as the result of culturing the keratinocyte in a keratinocyte medium in said (a). Specifically, the time point may be when the cell is cultured at about 90 to about 100% confluency. By exchanging the medium to a calcium medium at the time point, differentiation of a keratinocyte may be stimulated so as to induce to form a sheet.

The step (i) of (b) may be culturing the keratinocyte in a calcium medium, in which calcium is added to a keratinocyte medium, for about 2 to 6 about days. The culture may be conducted for about 2 to about 3 days. Culturing for the above culture time may help effective differentiation of the keratinocyte, i.e., forming a cultured epithelial cell layer. The culture in a calcium medium also may be conducted at an incubator of about 35 to about 37° C. and about 5 to about 10% $CO_2$.

The step (ii) may be culturing the cell by washing the keratinocyte cultured in a calcium medium with a buffer or a keratinocyte medium so as to remove calcium, and then adding a keratinocyte medium thereto again. The buffer is not particularly limited, and for example, it may be Phosphate Buffered Saline (PBS, pH 7.4) and/or Hank's Buffered Salt Solution (HBSS, pH 7.4). The cell also may be washed with a keratinocyte medium several times instead of washing with a buffer. The washed cell may be additionally cultured in a keratinocyte medium for another about 3 to about 7 days.

In the step (iii), the medium may be removed when the color of the newly exchanged medium is not changed any more. The medium may be removed within the additional culture time of about 3 to about 7 days. After removing the medium, the cell may be washed with a buffer and then incubated. The buffer used for washing may be, for example, PBS. The incubation may be conducted by covering the washed cell with the lid, and then storing in an incubator for about 5 to about 10 min. By incubating for the above time, the keratinocyte may be easily separated in the form of a cultured epithelial cell layer.

In the step (iv), the cultured epithelial cell layer may be spontaneously separated in a sheet form in the process adding a buffer or a keratinocyte medium again to the incubated cell. The buffer may be PBS, for example.

The step (c) may be collecting the cell attached to the bottom of a dish after the keratinocyte is removed in the step (b), and then culturing the cell in a melanocyte medium or a melanoblast medium.

In the step (c), after removing the cultured epithelial cell layer, the dish may be washed several times with PBS and then treated with accutase (Millipore; Cat. No., SCR005) for about 3 to about 10 min. The separated cell is precipitated by centrifugation, and then transferred to a general culture dish or a dish coated with gelatin, for example, 0.1% gelatin. Since then, the cell may be cultured by using a melanocyte medium. The melanocyte medium may be basal medium supplemented with supplements, wherein the basal medium comprises essential and non-essential amino acids, vitamins, organic compounds, trace minerals and inorganic salts, but do not comprise antibiotics, antimycotics, hormones, growth factors or proteins, wherein the supplements comprise fetal bovine serum, basic fibroblast growth factor, bovine pituitary extract, DMSO, heparin, hydrocortisone, insulin, transferrin and phorbol 12-myristate 13-acetate (PMA). For example, it may be M254 (Cascade Biologics, Cat. No.: M-254-500) medium supplemented with human melanocyte growth supplement (HMGS; Cascase Biology; Cat. No.: S-002-5). When the cell density becomes about 70 to about 90%, the cell may be subcultured.

In the step (c), after removing the cultured epithelial cell layer, the dish may be washed several times with PBS, and then treated with accutase (Millipore; Cat. No., SCR005) for about 3 to about 10 min. After precipitating the separated cell by centrifugation, the cell may be transferred to a general culture dish or a dish coated with gelatin, for example, 0.1% gelatin. Since then, the cell may be cultured by using a melanoblast medium. The melanoblast medium may be basal medium supplemented with supplements, wherein the basal medium comprises essential and non-essential amino acids, vitamins, organic compounds, trace minerals and inorganic salts, but do not comprise antibiotics, antimycotics, hormones, growth factors or proteins, wherein the supplements comprise fetal bovine serum, basic fibroblast growth factor, bovine pituitary extract, heparin, hydrocortisone, insulin, transferrin and endothelin-1. For example, it may be M254 (Cascade Biologics, Cat. No.: M-254-500) medium supplemented with human melanocyte growth supplement-2 (HMGS-2, PMA-free; Cascase Biology; Cat. No.: S-016-5). When the cell density becomes about 70 to about 90%, the cell may be subcultured.

Or, in the step (c), after removing the cultured epithelial cell layer, the dish is washed with PBS, the M254 medium supplemented with HMGS-2 is added thereto right after for additional culture, and then the cell may be transferred to a new dish when the cell density becomes about 70 to about 90% and then the cell may be cultured.

The keratinocyte-adapted melanocyte according to one embodiment of the present disclosure may be a melanocyte, which has at least one characteristic selected from the following characteristics: (i) an expression level of p75NTR, which is a neural crest stem cell marker lower than a primary melanocyte; (ii) an expression level of BRN2, which is expressed in a melanoblast higher than a primary melanocyte; (iii) a melanin content higher than a primary melanocyte; (iv) a tyrosinase activity higher than a primary melanocyte; (v) an increased expression level of p75NTR higher than a primary melanocyte when cultured in a phorbol 12-myristate 13-acetate (PMA)-free medium; (vi) lower increased expression level of BRN2 than a primary melanocyte when cultured in a PMA-free medium; (vii) a characteristic that a relative ratio of the p75NTR expression level of the keratinocyte-adapted melanocyte cultured in a PMA-free medium, to the p75NTR expression level of the keratinocyte-adapted melanocyte cultured in a PMA-containing melanocyte medium, is equivalent to about 60 to about 160% of the ratio of the p75NTR expression level of the primary melanocyte cultured in a PMA-containing melanocyte medium, to the p75NTR expression level of the keratinocyte-adapted melanocyte cultured in a PMA-containing melanocyte medium; (viii) a characteristic that a relative ratio of the BRN2 expression level of the keratinocyte-adapted melanocyte cultured in a PMA-free medium, to the BRN2 expression level of the keratinocyte-adapted melanocyte cultured in a PMA-containing melanocyte medium, is equivalent to about 1 to about 10 times of the ratio of the BRN2 expression level of the keratinocyte-adapted melanocyte cultured in a PMA-containing melanocyte medium, to the BRN2 expression level of the primary melanocyte cultured in a PMA-containing melanocyte medium; and (ix) a ratio of the cell attached to the bottom of a dish after 2 hour subculture higher than a primary melanocyte.

The expression level of p75NTR of (i) may be about $1/10$ time lower than the primary melanocyte. Further, the expression level of p75NTR of (i) may be about $1/20$, $1/30$, $1/40$, $1/50$, $1/60$ or $1/70$ time lower than the primary melanocyte. Further, the expression level of p75NTR of (i) may be about $1/10$ to about $1/1000$ time lower than the primary melanocyte. Further, the expression level of p75NTR of (i) may be about $1/20$ to about $1/500$ time, about $1/30$ to about $1/280$ time, about $1/40$ to about $1/190$ time or about $1/50$ to about $1/140$ time lower than the primary melanocyte. Due to this difference on the expression level, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

The expression level of BRN2 of (ii) may be about 5 times higher than the primary melanocyte. Further, the expression level of BRN2 of (ii) may be about 10 time or about 15 times higher than the primary melanocyte. Further, the expression level of BRN2 of (ii) may be about 5 times to about 50 times, about 10 times to about 40 times, about 15 times to about 30 times or about 16 times to about 20 times higher than the primary melanocyte. Due to this difference on the expression level, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

The melanin content of (iii) may be about 2 times or higher than the primary melanocyte. Further the melanin content of (iii) may be about 3 times or about 4 times higher than the primary melanocyte. Further, melanin content of (iii) may be about 2 times to about 10 times, about 3 times to about 5 times or about 3 times to about 4 times higher than the primary melanocyte. Due to this difference on the content, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

The tyrosinase activity of (iv) may be about 2 times or more, about 4 times or more, or about 8 times or more higher than the primary melanocyte when incubated at 37° C. for about 120 min. Further, it may be about 2 times to about 32 times, about 4 times to about 16 times, or about 6 times or about 10 times than the primary melanocyte. Due to this difference on the activity, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

The expression level of (v) may be 2 times or more of the expression level of the primary melanocyte. Further, the expression level of (v) may be about 2 times to about 18 times, about 3 times to about 10 times, or about 4 times to about 8 times of the expression level of the primary melanocyte. Due to this difference on the expression level, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

The expression level of (vi) may be about $9/10$ to about $1/10$ time of the expression level of the primary melanocyte. Further, the expression level of (vi) may be about $7/10$ to about $3/10$ time of the expression level of the primary melanocyte. Due to this difference on the expression level, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

In the expression level of (vii), the relative ratio of the p75NTR expression level of the keratinocyte-adapted melanocyte cultured in a PMA-free medium, to the p75NTR expression level of the keratinocyte-adapted melanocyte cultured in a PMA-containing melanocyte medium, may be equivalent to about 60 to about 160%, about 80 to about 140% or about 90 to about 130% of the ratio of the p75NTR expression level of the primary melanocyte cultured in a PMA-containing melanocyte medium, to the p75NTR expression level of the keratinocyte-adapted melanocyte cultured in a PMA-containing melanocyte medium. Due to this difference on the expression level, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

In the expression level of (viii), the relative ratio of the BRN2 expression level of the keratinocyte-adapted melanocyte cultured in a PMA-free medium, to the BRN2 expression level of the keratinocyte-adapted melanocyte cultured in a PMA-containing melanocyte medium, is equivalent to about 1 to about 10 times, about 2 to about 8 times, about 3 to about 7 times or about 4 to about 6 times of the ratio of the BRN2 expression level of the keratinocyte-adapted melanocyte cultured in a PMA-containing melanocyte medium, to the BRN2 expression level of the primary melanocyte cultured in a PMA-containing melanocyte medium. Due to this difference on the expression level, the characteristic of the keratinocyte-adapted melanocyte according to one embodiment of the present disclosure, for example, ability of keeping melanin forming capacity without a keratinocyte as well as better homogeneity and proliferation capacity, compared with the primary melanocyte, may be maximized.

The ratio of the cell attached to the bottom of a dish after about 2 hour subculture of (ix) may be about 80% or more. The ratio of the cell attached to the bottom of a dish after about 2 hour subculture of (ix) may be about 90% or more. The ratio of the cell attached to the bottom of a dish after about 2 hour subculture of (ix) may be about 95% or more. The keratinocyte-adapted melanocyte according to one embodiment of the present disclosure may be the cell derived from a keratinocyte. In particular, it may be the cell derived from a human keratinocyte.

The keratinocyte-adapted melanocyte according to another embodiment of the present disclosure may be the cell produced by any one method described above.

The keratinocyte-adapted melanocyte according to one preferred embodiment of the present disclosure is KCTC (Korean Collection for Type Culture) as an International Depositary Authority under the Budapest Treaty on Sep. 14, 2011, as Accession No. KCTC 12015BP.

The melanoblast, which is separated from the culture of a keratinocyte, according to one embodiment of the present disclosure may be the keratinocyte-adapted melanoblast, and may have a characteristic that the expression level of at least one melanoblast marker selected from the group consisting of MITF, DCT, TYRP1, SNAI2, C-KIT and EDNRB is higher than a primary melanocyte or a keratinocyte-adapted melanocyte.

In another embodiment of the present disclosure, the melanoblast may have a characteristic that the expression level of at least one melanoblast marker selected from MITF and DCT is about 2 times or more, about 3 times or more, about 4 times or more, or about 5 times or more higher than a primary melanocyte or a keratinocyte-adapted melanocyte. Such high expression level may be a distinctive characteristic, which may distinguish the melanoblast described in this description from a primary melanocyte or a keratinocyte-adapted melanocyte (KaMC).

Further, in one embodiment, the melanoblast may be the cell having at least one characteristic selected from higher BRN2 protein expression level and lower TYR protein expression level, than the keratinocyte-adapted melanocyte.

In another embodiment, the melanoblast may be the cell showing the cell number increased about 20 times or more, about 25 times or more, about 30 times or more, or about 35 times or more than the initial cell number when cultured in a melanoblast medium for about 9 days. Such high cell proliferation rate may be a distinctive characteristic, which may distinguish the melanoblast described in this description from a primary melanocyte or a keratinocyte-adapted melanocyte (KaMC).

In further another embodiment, the melanoblast may be the cell continuously growing even when subcultured about 6 times or more, about 7 times or more, about 8 times or more, or 9 times or more in a melanoblast medium. Such characteristic of maintaining the cell proliferation capacity for a long time may be a distinctive characteristic, which may distinguish the melanoblast described in this description from a primary melanocyte or a keratinocyte-adapted melanocyte (KaMC).

The keratinocyte-adapted melanoblast according to one embodiment of the present disclosure may be the cell derived from a keratinocyte. In particular, it may be the cell derived from a human keratinocyte.

The keratinocyte-adapted melanoblast according to another embodiment of the present disclosure may be the cell produced by any one method described above.

The keratinocyte-adapted melanoblast according to one preferred embodiment of the present disclosure is KCTC (Korean Collection for Type Culture) as an International Depositary Authority under the Budapest Treaty on Jul. 24, 2012, as Accession No. KCTC 12250BP.

The examples (and experiments) will now be described. The following examples (and experiments) are for illustrative purposes only and not intended to limit the scope of the present disclosure.

MODE FOR INVENTION

Example

1. Production of Keratinocyte-Adapted Melanocyte (a) Step of Culturing Keratinocyte As a human keratinocyte (Normal Human Epidermal Keratinocytes), NHEK-Neo, Pooled (Neonatal Normal Human Epidermal Keratinocytes, Pooled: Cat. No. 00192906) from Lonza is used. As a keratinocyte medium for culturing the human keratinocyte, KGM-GOLD™ BULLETKIT™ (keratinocyte growth medium kit including supplements and growth factors in separate aliquots) £Cat. No. 192060; Lonza) is used. In order to maintain a characteristic that a keratinocyte is attached to a base membrane and proliferates, a dish coated with 10 μg/ml collagen type I is used. The cell is cultured in a 37° C., 5% $CO_2$ incubator, and subcultured when the cell density becomes about 70%. For inducing the keratinocyte to a cultured epithelial cell layer, KGM™-2 BULLETKIT™ (keratinocyte growth medium kit including supplements and growth factors in separate aliquots) (Cat. No. CC-3107; Lonza) and 0.1% gelatin coating are used.

(b) Step of Removing Keratinocyte

In order to remove the keratinocyte from the dish in the form of a sheet, a cultured epithelial cell layer, a calcium medium, in which calcium is finally added at high concentration, i.e., 1.2 mM $CaCl_2$, to a keratinocyte medium, is used. The culture in the calcium-enriched medium is also conducted at the same 37° C., 5% $CO_2$ incubator. The keratinocyte medium is exchanged with a calcium-enriched medium at the time point when the keratinocyte is cultured until the cell covers the bottom of the culture dish (about 90% confluency), and then cultured for 3 days. The cultured keratinocyte is washed three times with Phosphate Buffered Saline (PBS, pH 7.4) to remove highly concentrated calcium, the medium is exchanged with a keratinocyte medium, and then the cell is additionally cultured for another 4 days. The medium is removed when the color of the newly exchanged medium is not changed any more within this period, and the cell is washed twice with PBS, covered with the lid, and then stored in the incubator for 5 min. During a process adding PBS again, the cultured epithelial cell layer is spontaneously separated. Right after the cultured epithelial cell layer is removed, there is a cell still remained at the bottom of the dish.

The remained cell is observed with a microscope, and its image is shown in FIG. 1(A). As shown in FIG. 1(A), the cell has a longish shape unlike the keratinocyte.

(c) Step of Collecting Cell Attached to Bottom of Dish from Keratinocyte-Removed Culture and Culturing them After removing the cultured epithelial cell layer, the dish is washed twice with PBS, and then treated with accutase (Millipore; Cat. No., SCR005) for 5 min. The separated cell is precipitated by centrifugation, and then transferred to a dish coated with 0.1% gelatin. Since then, M254 (Cascade Biologics, Cat. No.: M-254-500) medium supplemented with human melanocyte growth supplement (HMGS; Cascase Biology; Cat. No.: S-002-5) is used. As a result, the cultured cell is observed with a microscope, and its image is shown in FIG. 1(B). As shown in FIG. 1(B), the cell has a bipolar shape.

When the cell density becomes about 80%, the cell is subcultured. The subcultured cell is observed with a microscope, and its image is shown in FIG. 1(C). As shown in FIG. 1(C), the melanocyte separated from a keratinocyte is possible to be subcultured, and has good proliferation capacity.

2. Characterization of Keratinocyte-Adapted Melanocyte (KaMC) Produced from Keratinocyte As a primary melanocyte (PMC) for comparison with the KaMC, NHEM-Neo (Neonatal normal human melanocytes, Cat. No. cc-2504) from Lonza is used.

(1) qPCR Analysis

The separated KaMC; NHEK-Neo, Pooled (Neonatal Normal Human Epidermal Keratinocytes, Pooled: Cat. No. 00192906) as a keratinocyte (Normal Human Epidermal Keratinocyte) (KC) from Lonza; and a primary melanocyte (PMC) are washed with PBS, respectively, and total RNA is isolated therefrom by using a kit (miRNeasy mini kit, Qiagen, Cat. No. 217004). Then, cDNA is synthesized by using a RT-PCR kit (SuperScript III First-Strand Synthesis System for RT-PCR, Invitrogen, Cat. No. 18080-051). Changes on mRNA expression of SOX10, PAX3, MITF, TYR, TYRP1, DCT, PMEL and NESTIN as a marker of the melanocyte lineage are measured by using the synthesized cDNA as a template, primers, which specifically bind to a gene (TAQMAN® (probe-based gene expression assay), Applied Biosystems), and SYBR (TAQMAN® (probe-based gene expression assay) Universal PCR Master Mix, Applied Biosystems; Cat. No., 4304437).

Figure 2:
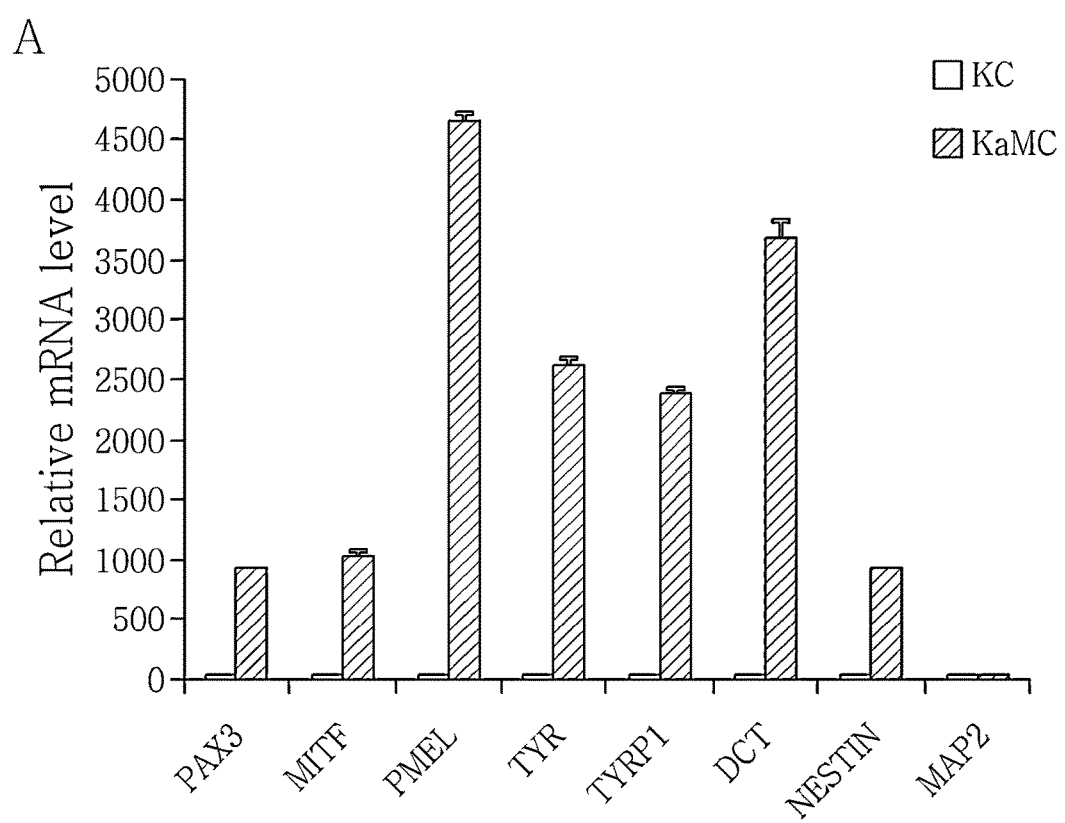
FIG. 2 and FIG. 3 are graphs comparing expression patterns of genes specific to the melanocyte adapted to a keratinocyte according to one embodiment of the present disclosure, i.e., melanocytes separated from keratinocytes (keratinocyte-adapted melanocyte, KaMC) (A,B), and genes specific to keratinocytes (C), with keratinocytes.

The result is shown in FIG. 2. As shown in FIG. 2, it is found that the KaMC expresses melanocyte-specific genes more than the keratinocyte (KC).

Figure 3:
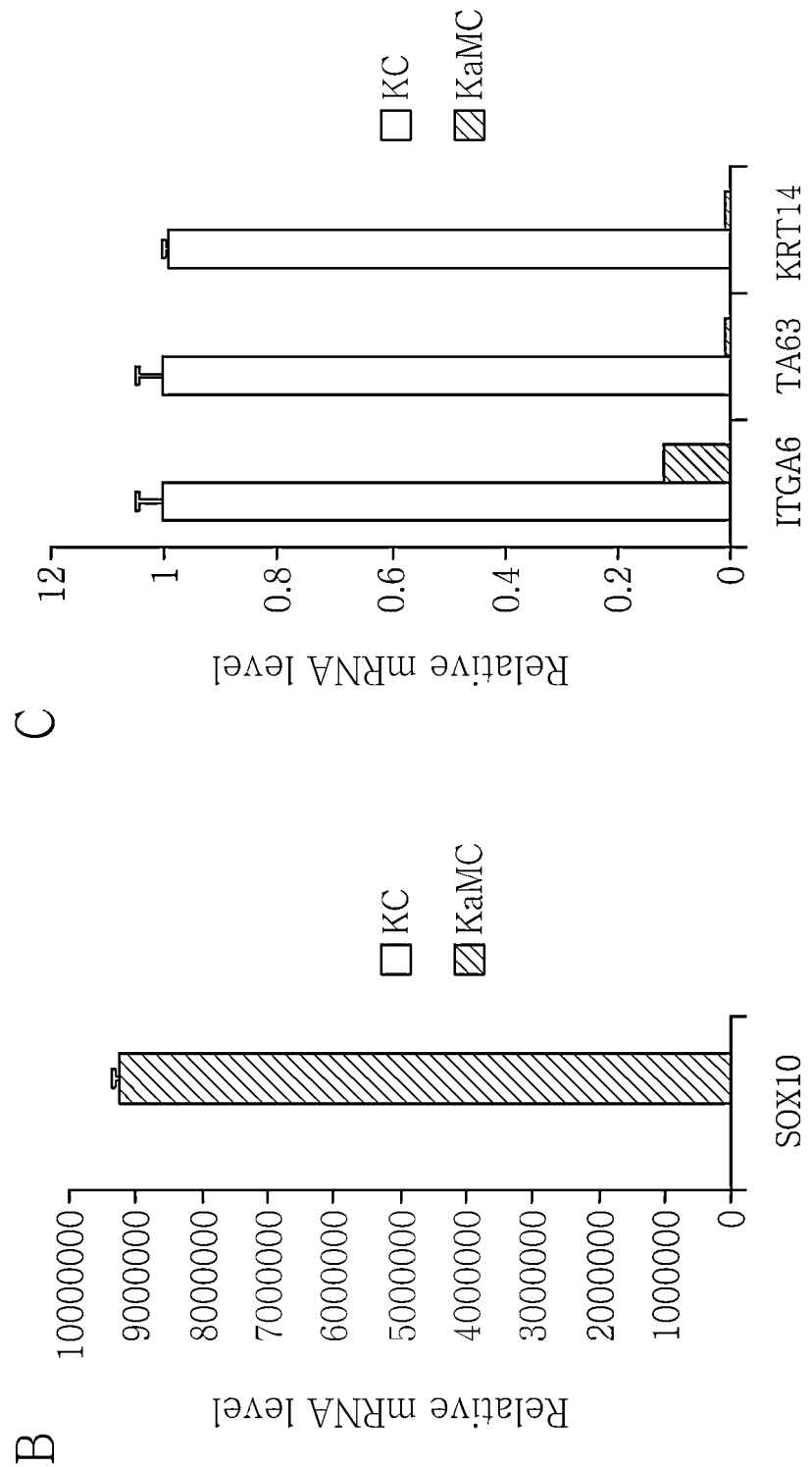

On the other hand, change on mRNA expression of SOX10 as a marker of the melanocyte lineage is measured. The result is shown in FIG. 3(B). As shown in FIG. 3(B), it is found that the KaMC expresses the SOX10 as a melanocyte-specific gene more than the keratinocyte (KC) as much as 9 million times.

On the other hand, changes on mRNA expression of ITGA6, TP63 and keratin14 (KRT14) as a marker of a keratinocyte are measured. As a result, the expression is significantly reduced in the KaMC, compared with the keratinocyte (KC) (FIG. 3(C)).

Figure 4:
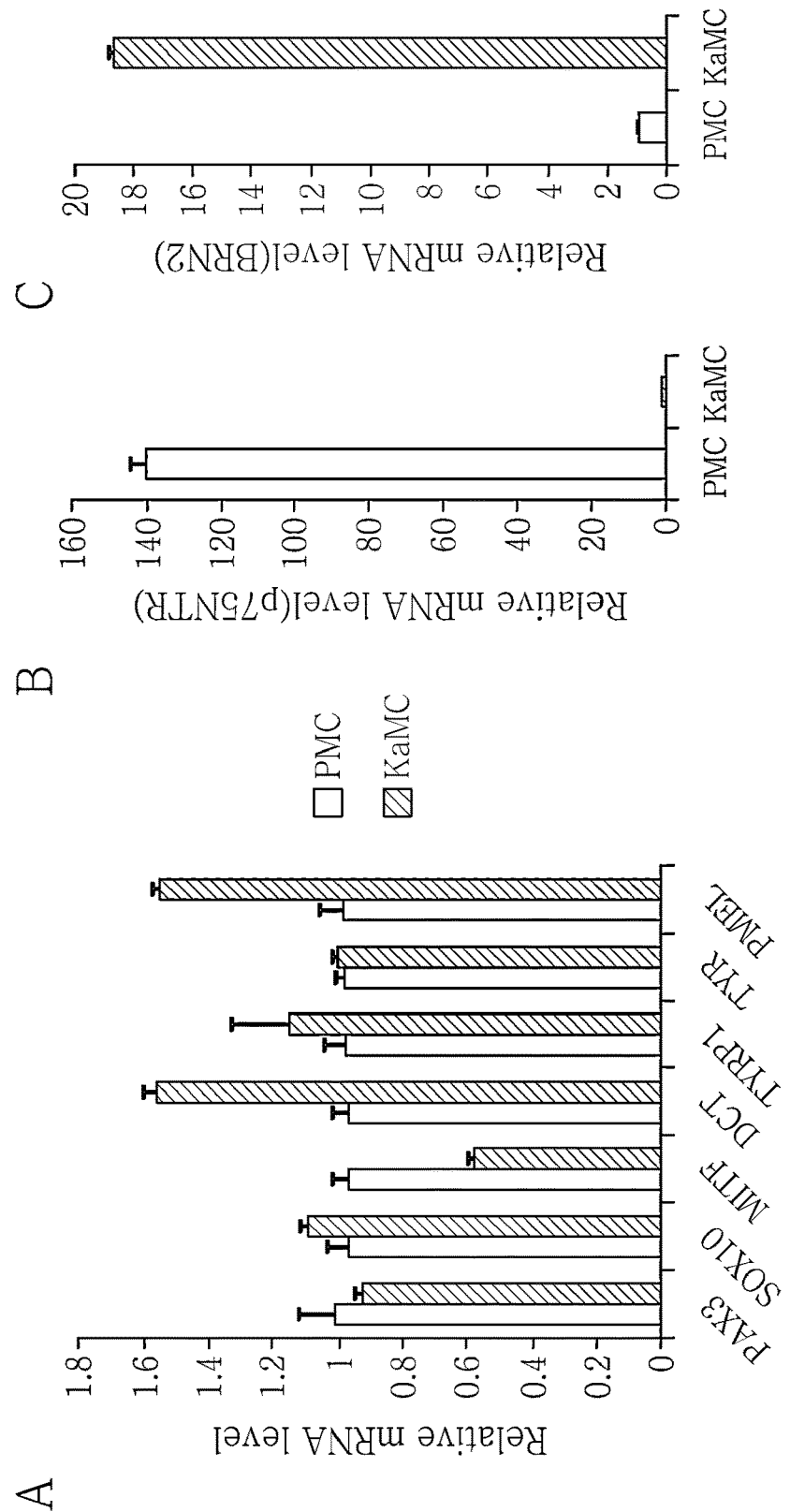
FIG. 4 is graphs comparing gene expression patterns in primary melanocyte (PMC) and KaMC.

Further, when comparing with the primary melanocyte (PMC), it is found that there is no difference on the expression levels of overall melanocyte-specific genes (FIG. 4(A)), but the p75NTR as a neural crest stem cell marker is overexpressed in the PMC (FIG. 4(B)) and the BRN2, which is known as being expressed in a melanoblast, is relatively highly expressed in the KaMC (FIG. 4(C)).

(2) Tyrosinase Activity Assay

After removing the medium, the cell is washed twice with PBS, and then a lysis buffer (Sigma) is added thereto so as to collect the cell. Protein in the cell is extracted while rocking at 4° C. for 1 hour, and then cell pellet and extract are separated from each other by centrifugation (1300 rpm, 15 min).

Figure 5:
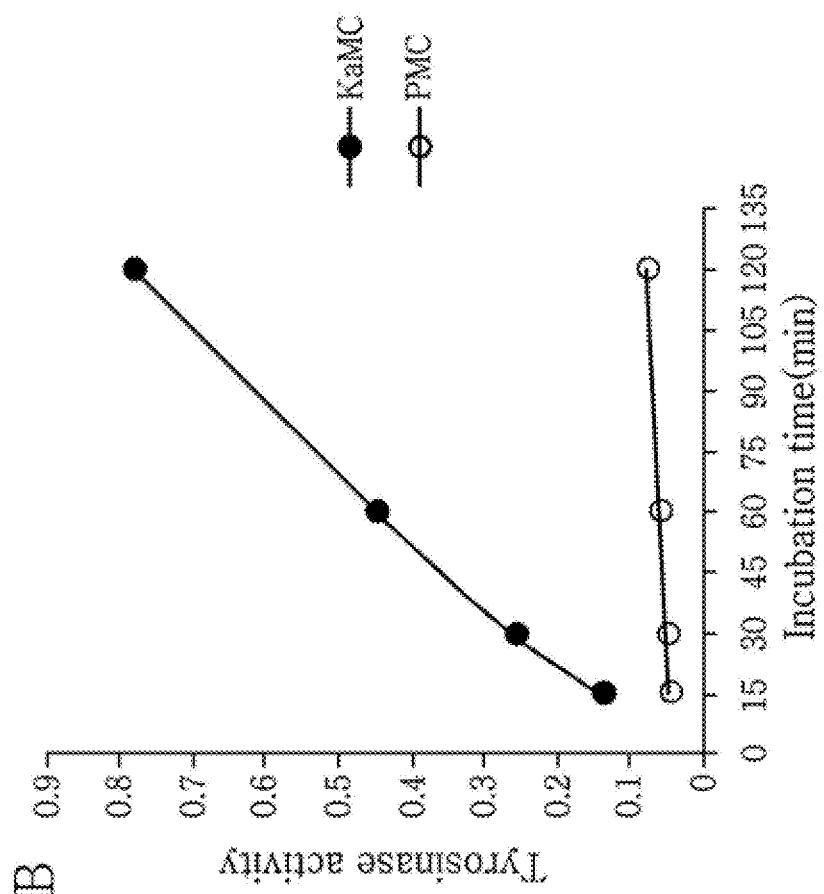
FIG. 5 is images comparing pellet color of PMC and KaMC (A) and a graph comparing tyrosinase activities thereof (B)

FIG. 5(A) is pictures of the pellet taken after separating the PMC and KaMC grown in a melanocyte medium. As shown in FIG. 5(A), it is found that the keratinocyte-adapted melanocyte (KaMC) according to one embodiment of the present disclosure contains more melanin than the primary melanocyte (PMC). Both of the cells are derived from white people. Accordingly, the difference on the melanin content is notable.

On the other hand, the separated extract is transferred to a new E-tube, and then protein quantification is conducted by using BCA (bicinchoninic acid) (Pierce, Cat. No.: 23227). A lysis buffer is added to 40 μg protein to the final volume of 100 μl in a 96-well plate, and then 100 μl L-Dopa (Sigma, Cat. No. D-9628, 2 mg/ml in 0.1M phosphate buffer, filtrated) is added thereto followed by reacting them at 37° C. for various time (15, 30, 60, 120 min). After each reaction time, absorbance is measured by using a microplate reader at 490 nm.

The result is shown in FIG. 5(B). As shown in FIG. 5(B), as the incubation time increases, the tyrosinase activity of the KaMC is gradually increased, and after incubated for 120 min, the tyrosinase activity of the KaMC is up to about 8 times higher than the PMC.

(3) Analysis of Reactivity to PMA

In order to check the effect of PMA, which induces differentiation of a melanocyte, M-254 medium supplemented with PMA-free HMGS-2 (Cascade Biologics, Cat. No.: S-016-5) is used for subculture (PMA−). The result is compared with the result from the cell cultured in M254 (Cascade Biologics, Cat. No.: M-254-500) medium supplemented with human melanocyte growth supplement (HMGS; Cascase Biology; Cat. No.: S-002-5) (PMA+). The result is shown in FIG. 6 and FIG. 7.

Figure 7:
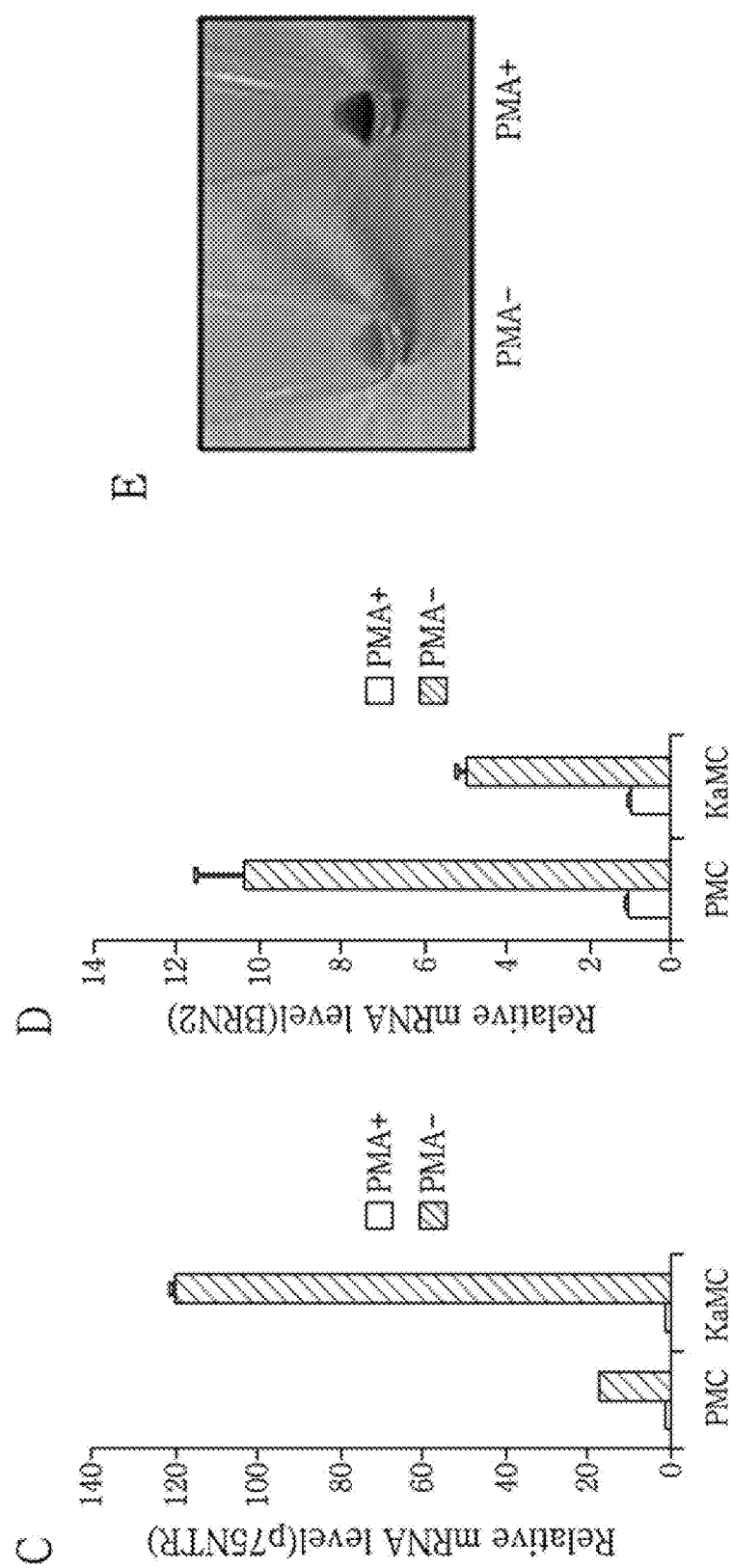
FIG. 7 is graphs showing change on expression of p75NTR and BRN2 in PMC and KaMC depending on the presence of PMA (C, D), and an image showing color change of pellet (E)

When adding the PMA− medium containing endothelin, which is known as dedifferentiating the differentiated melanocyte, there is little difference on the expression levels of the melanocyte-specific genes in the PMC and the KaMC (FIGS. 6(A and B)), but when cultured in the PMA− medium, the expression level of the p75NTR in the KaMC and the expression level of the BRN2 in the PMC are highly increased, compared with the result when cultured in the PMA+ medium (FIGS. 7(C and D)). In particular, the ratio of the p75NTR expression level in the KaMC cultured in the PMA− medium, to the p75NTR expression level in the KaMC cultured in the PMA+ medium, is increased to the similar level with the ratio of the p75NTR expression level in the PMC, to that in the KaMC cultured in the PMA+ medium (FIG. 4(B)) (FIG. 7(C)). Further, the ratio of the BRN2 expression level in the PMC cultured in the PMA− medium, to the BRN2 expression level in the PMC cultured in the PMA+ medium, is increased to the similar level with the ratio of the BRN2 expression level in the KaMC, to that in the PMC cultured in the PMA+ medium (FIG. 4(C)) (FIG. 7(D)).

In addition, as a result of the culture in the PMA− medium, it is observed that the color of the KaMC pellet also becomes light (FIG. 7(E)). This refers that the KaMC forms more pigment than the PMC, and this pigment formation may be controlled depending on the presence of the PMA, a material inducing melanocyte differentiation.

In short, it is expected that the differentiation and dedifferentiation of a melanocyte may be induced by controlling the expressions of the p75NTR and the BRN2, and the pigment formation may be also controlled by the same way.

(4) Comparison of Initial Engraftment Capacity and Viability, and Cell Proliferation Capacity In order to check engraftment capacity and viability at the early stage of subculture, the state of the cell after subculturing at the same condition for 2 hours is observed. Specifically, the KaMC and the PMC are transferred to a dish coated with 0.1% gelatin, and then cultured in M254 (Cascade Biologics, Cat. No.: M-254-500) medium supplemented with human melanocyte growth supplement (HMGS; Cascase Biology; Cat. No.: S-002-5) at 37° C. for 2 hours. The result is shown in FIG. 8(A). As shown in FIG. 8(A), it is found that in the case of the KaMC, 95% or more cells are attached to the bottom of the dish within 2 hours, thereby forming a shape with stretched dendrites, but in the case of the PMC, the cells are not attached well and most of the cells are floating at the same period. In FIG. 8(A), arrows indicate the floating cells.

On the other hand, in order to check engraftment capacity, viability and cell proliferation capacity, ELISA using BrdU (Roche, Cat. No.: 11647229001) is used. The cell number is counted by using 0.4% trypan blue staining and a cell counter. Both of the PMC and the KaMC are plated with the same cell number ($3 \times 10^4$). Nonetheless, it is found that the number of the PMC labeled with BrdU of 1 day post plating becomes much lower than the KaMC (FIG. 8(B)). There is little difference on the doubling time. Accordingly, good proliferation capacity of the KaMC as shown in FIG. 1(C) indicates that there are many cells having excellent engraftment capacity and viability, and proliferating and having ability to proliferate, during subculture.

3. Production of Keratinocyte-Adapted Melanoblast (KaMB)

(a) Step of Culturing Keratinocyte

A Human keratinocyte is cultured with the same method described in 1.(a).

(b) Step of Removing Keratinocyte

The keratinocyte is separated in a sheet form with the same method described in 1. (b). As a result, there are still some cells remained at the bottom of a dish.

Figure 9:
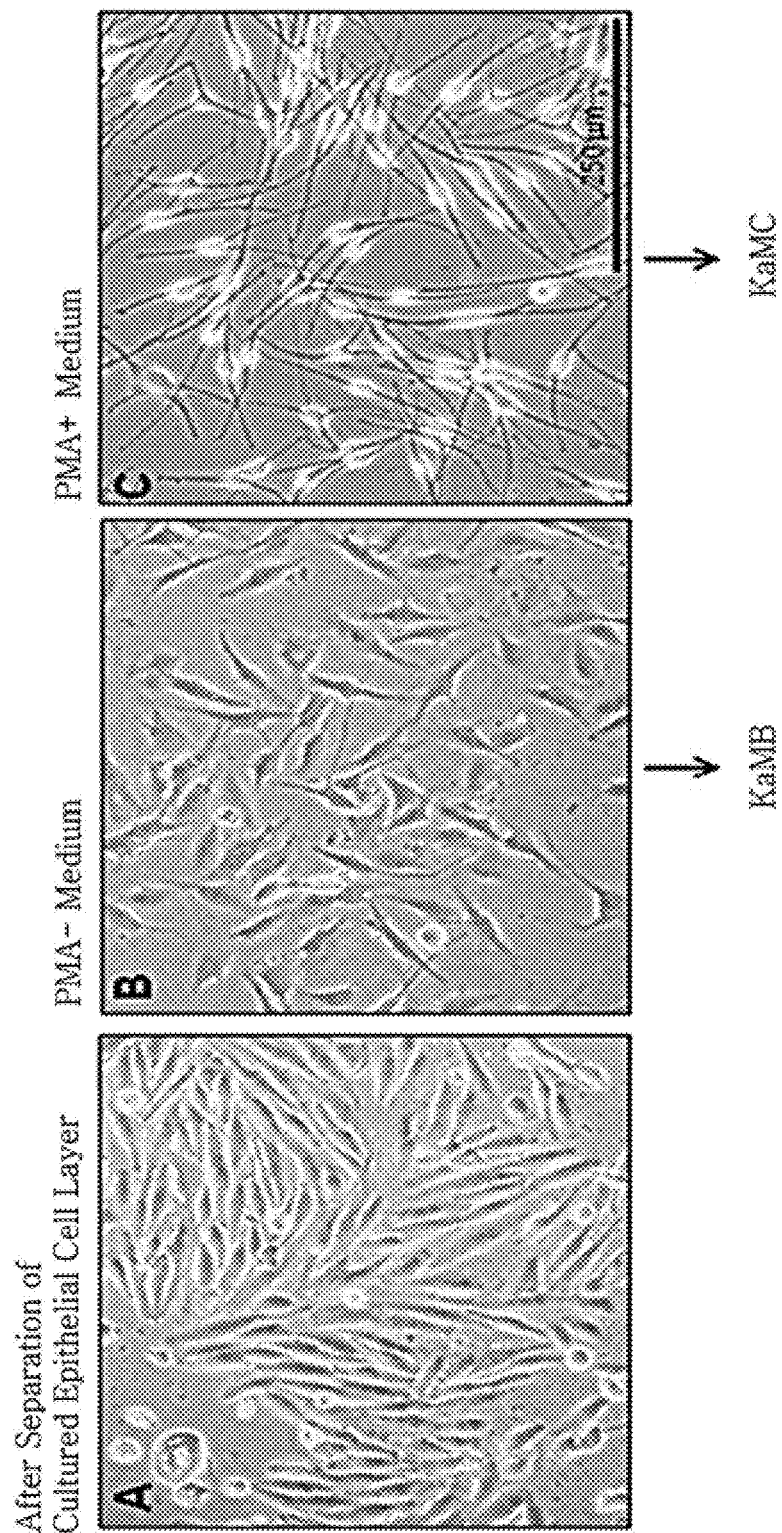
FIG. 9 are images showing cells remained in the bottom of a dish right after separating a cultured cell layer (A), the cells, which are remained in the bottom of a dish, growing in a PMA− melanoblast medium (B), and melanocytes growing in a PMA+ melanocyte medium after subculturing the cells of (B) (C) (Scale bar, 250 μm)

The remained cell is observed with a microscope, and its image is shown in FIG. 9(A). As shown in FIG. 9(A), the cell has a longish shape unlike the keratinocyte.

(c) Step of Collecting Cell Attached to Bottom of Dish from Keratinocyte-Removed Culture and Culturing them After removing the cultured epithelial cell layer, the dish is washed twice with PBS, and then treated with accutase (Millipore; Cat. No., SCR005) for 5 min. The separated cell is precipitated by centrifugation, and then transferred to a new dish. Since then, M254 (Cascade Biologics, Cat. No.: M-254-500) medium supplemented with human melanocyte growth supplement-2 (HMGS-2, PMA-free; Cascase Biology; Cat. No.: S-016-5) is used. As a result, the cultured cell is observed with a microscope, and its image is shown in FIG. 9(B). When the cell density becomes about 80%, the cell is subcultured. When the cell of FIG. 9(B) is cultured in a melanocyte medium (M254/HMGS) supplemented with PMA, a representative material for inducing melanocyte differentiation, it shows a bipolar shape (FIG. 9(C)).

4. Characterization of Keratinocyte-Adapted Melanoblast (KaMB) Produced by Culturing Keratinocyte As a primary melanocyte (PMC) for comparison with the KaMB, NHEM-Neo (Neonatal normal human melanocytes, Cat. No. cc-2504) from Lonza is used. Further, a keratinocyte-adapted melanocyte (KaMC) for comparison with the KaMB is also prepared. The KaMC is obtained by the same method with the KaMB except for culturing the cell separated in the step (c) in M254 (Cascade Biologics, Cat. No.: M-254-500) medium supplemented with human melanocyte growth supplement (HMGS; Cascase Biology; Cat. No.: S-002-5). Further, the cell is cultured in a PMA+ medium and a PMA− medium, respectively.

(1) qPCR Analysis

The separated KaMB, KaMC and a primary melanocyte (PMC) are washed with PBS, respectively, and total RNA is isolated therefrom by using a kit (miRNeasy mini kit, Qiagen, Cat. No. 217004). Then, cDNA is synthesized by using a RT-PCR kit (SuperScript III First-Strand Synthesis System for RT-PCR, Invitrogen, Cat. No. 18080-051). Changes on mRNA expression of NOTCH1, SOX10, PAX3, EDNRB, 15 c-KIT, SNAI2, MITF, DCT, TYRP1, TYR and PMEL as a marker of the melanoblast/melanocyte lineage are measured by using the synthesized cDNA as a template, primers, which specifically bind to a gene (TAQMAN® (probe-based gene expression assay), Applied Biosystems), and SYBR (TAQMAN® (probe-based gene expression assay) Universal PCR Master Mix, Applied Biosystems; Cat. No., 4304437).

Figure 10:
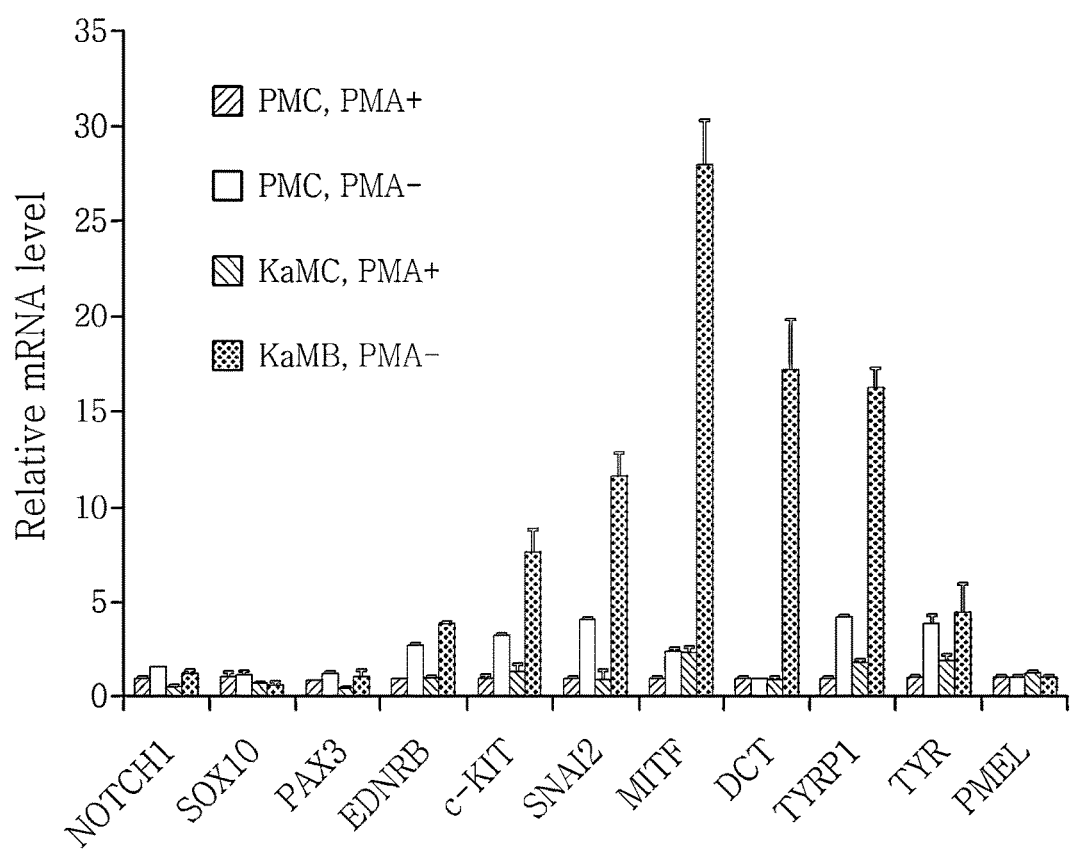
FIG. 10 is a graph comparing expression level of each gene in each cell depending on the presence of PMA.

The result is shown in FIG. 10. As shown in FIG. 10, it is found that, as a result of RT-qPCR of the KaMB, it expresses the melanoblast markers such as EDNRB, c-KIT, SNAI2, MITF, DCT and TYRP1 relatively more than the PMC cultured in the PMA− or PMA+ medium and the KaMC cultured in the PMA+ medium.

(2) Tyrosinase Activity Assay

After removing the medium, the cell is washed twice with PBS, and then a lysis buffer (Sigma) is added thereto so as to collect the cell. Protein in the cell is extracted while rocking at 4° C. for 1 hour, and then cell pellet and extract are separated from each other by centrifugation (1300 rpm, 15 min).

Figure 11:
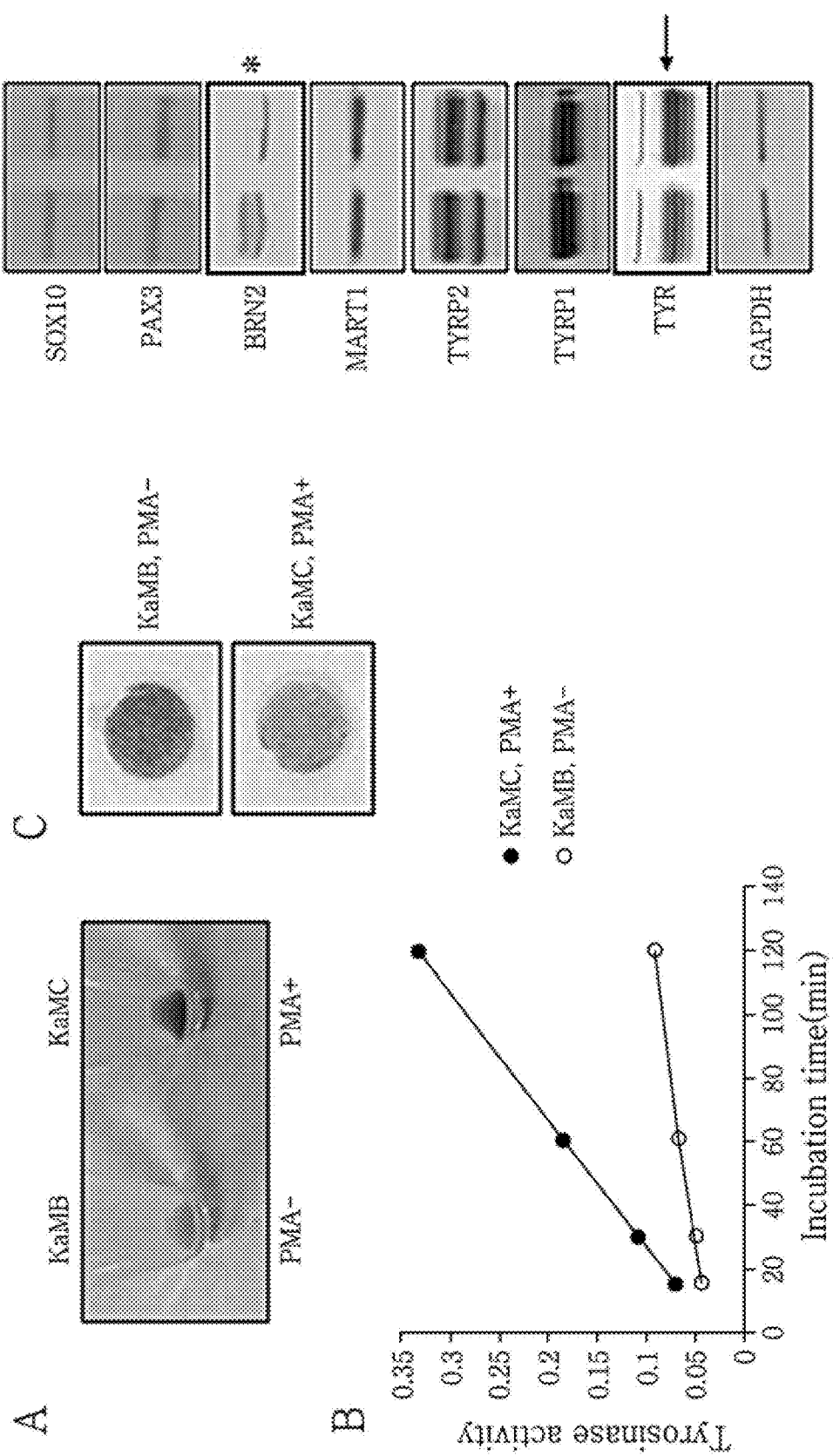
FIG. 11 is an image comparing pellet color of KaMB cultured in a PMA−medium and KaMC cultured in PMA+ medium (A), a graph comparing tyrosinase activities of the above cells (B), images comparing cell mobilities of the above cells (C), and images comparing expression levels of various proteins in the above cells (D)

FIG. 11(A) is pictures of the pellet taken after separating the KaMB grown in the medium, which does not contain PMA, a melanocyte differentiation inducing material, and the KaMC, which is derived from the KaMB grown in the PMA-containing medium. From this, it is found that the KaMB may be differentiated to a melanocyte, which may form pigment at a PMA-containing condition.

On the other hand, the separated extract is transferred to a new E-tube, and then protein quantification is conducted by using BCA (bicinchoninic acid) (Pierce, Cat. No.: 23227). A lysis buffer is added to 40 μg protein to the final volume of 100 μl in a 96-well plate, and then 100 μl L-Dopa (Sigma, Cat. No. D-9628, 2 mg/ml in 0.1 M phosphate buffer, filtrated) is added thereto followed by reacting them at 37° C. for various time (15, 30, 60, 120 min). After each reaction time, absorbance is measured by using a microplate reader at 490 nm.

The result is shown in FIG. 11(B). As shown in FIG. 11(B), as the incubation time increases, the tyrosinase activity of the KaMC is increased, compared with the KaMB.

(3) Cell Mobility Analysis

Each type of cell (5×10$^4$) is seeded in a cell culture insert (Becton Dickinson, Cat. No.: 353097, pore size: 8.0 mm) coated with collagen I (final concentration: 10 µg/ml), and then cultured in a 24-well for 4 hours. After removing the medium, the cell is fixed with methanol for about 5 to 10 min. Cell nucleus is stained with hematoxylin for 5 min and washed several times with water, and then soaked in eosin for about 1 to 5 min for cytoplasm staining. After washing several times with water, excess water is clearly drained from the inside of the insert using a cotton swab. Only a filter is removed from the insert using a knife, and then mounted on a slide glass. The result is shown in FIG. 11(C). As a result of checking the cell migration using a transwell, the KaMB shows dominant migration within 4 hours, compared with the differentiated KaMC. According to the fact that a melanoblast has cell mobility as a characteristic of a developmental process in a living body, it is confirmed that the KaMB has the melanoblastic characteristic.

(4) Protein Expression Analysis

When the KaMB and the KaMC are cultured in a 100-mm dish, respectively, and the cell density becomes about 80 to 90%, the cell is washed twice with PBS. Then a lysis buffer (Sigma) about 100 to 150 µl is added thereto, and the cell is collected using a cell scraper (SPL Life Sciences). The cell is incubated in a low temperature refrigerator (4 to 8° C.) for 10 min, centrifuged for 10 min. Then, a supernatant containing various proteins is transferred to a new tube, and protein quantification is conducted by using a BCA protein assay kit (Thermo Scientific; Cat. No. 23227). 15 µg protein is electrophoresed and transferred to a nitrocellulose membrane, and then western blot is conducted by using each antibody, SOX10 (R&D systems, MAB2864), PAX3 (R&D systems, MAB2457), BRN2 (ProteinTech Group, 14596-1-AP), MART1 (Thermo Scientific, MS-716), TYRP2 (Santa Cruz biotechnology, C-9, sc-74439), TYRP1 (Santa Cruz biotechnology, H-90, sc-25543), TYR (Santa Cruz biotechnology, H-109, sc-15341) and GADPH (Santa Cruz biotechnology, FL-335, sc-25778). As a result, specific BRN2 expression is observed in the KaMB (FIG. 11(D), asterisk), and it is found that the expression of tyrosinase (TYR), an essential protein for forming melanin, is increased in the KaMC (FIG. 11(D), arrow). The BRN2 is a marker of a human melanoblast, and it is confirmed that the KaMB separated from the keratinocyte culture is a melanoblast.

(5) Analysis of Reactivity to PMA

In order to check whether the melanoblastic characteristic is resulted from dedifferentiation simply caused by medium exchange or not, the primary melanocyte and the KaMB are cultured in a melanocyte medium containing PMA, a melanocyte differentiation inducing material, and a melanoblast medium not containing PMA, respectively. As a result, the primary melanocyte is properly grown in the PMA-containing medium, but is hardly grown in the melanoblast medium not containing PMA (FIG. 12(A), 3$^{rd}$, 4$^{th}$ panels). On the contrary, the KaMB separated from a keratinocyte shows superior proliferation capacity in the melanoblast medium not containing PMA than in the PMA-containing melanocyte medium (FIG. 12(A), 1$^{st}$, 2$^{nd}$ panels). From this result, it is found that the KaMB is the cell having different characteristics from the dedifferentiated cells, which may be obtained by simply culturing in a melanoblast medium.

(6) Cell Growth Curve

Each type of cell is seeded in 5 wells of a 24-well plate at the concentration of 3.4×10$^4$ cells per well, and the cell number is measured at 0, 3, 6, 9 and 12$^{th}$ day, respectively. As a result, the KaMB cell shows the highest proliferation capacity (FIG. 12(B))

(7) Analysis of Cell Division Capacity

Figure 13:
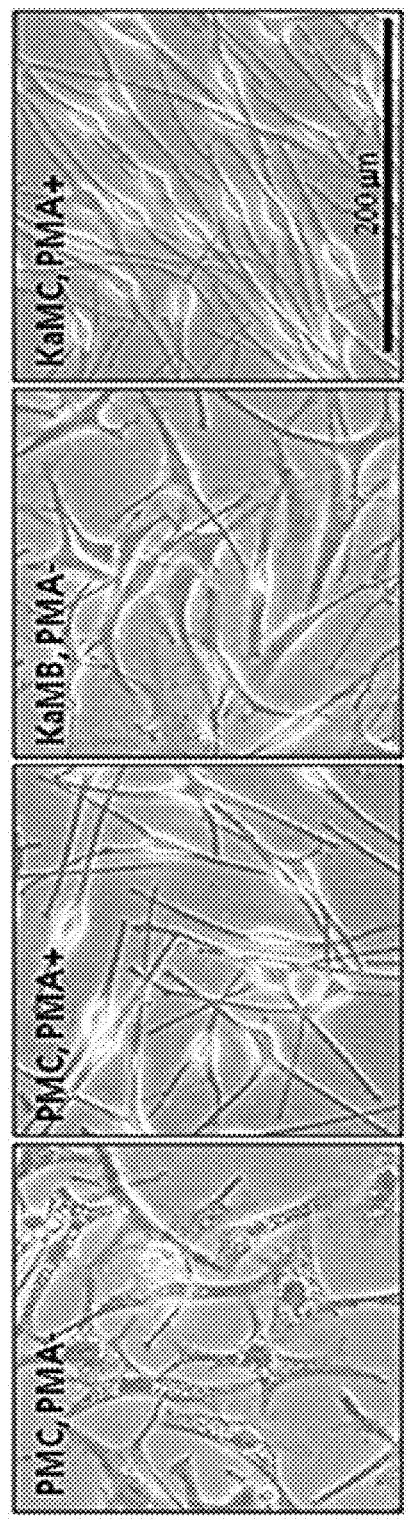
FIG. 13 is images of state of each cell cultured for a long time in a PMA− or PMA+ medium (Scale bar, 200 μm).

Each cell is seeded in each well of a 96-well plate at the concentration of 1×10$^4$ cells per well, and cultured for 3 days. Then, the cell is labeled using Cell Proliferation ELISA, BrdU kit (Roche, Cat. No.: 11 647 229 001), and absorbance is measured with 10, 20 and 30 min interval. The BrdU has a characteristic of being attached to DNA of a dividing cell. As a result, it is found that the KaMB in the melanoblast medium not containing PMA divides and proliferates the most (FIG. 12(C)). There is no big change while culturing the KaMB in the medium not containing PMA for a long time (passage 9) (FIG. 13, 3$^{rd}$ panel), but the primary melanocyte hardly proliferates in this medium and also form many vacuoles in the cell when cultured for a long time (passage 6) (FIG. 13, 1$^{st}$ panel). Even when the KaMC and the PMC are cultured in the PMA-containing melanocyte medium, respectively, the KaMC shows better proliferation capacity than the PMC (FIG. 12(B,C)).

From such test result, the KaMB separated from the keratinocyte culture shows the best proliferation capacity in the PMA- melanoblast medium, specifically expresses gene markers and proteins of a melanoblast, and may be differentiated to a melanocyte by PMA, a differentiation inducing material. Thus, it is a melanoblast. Further, it is found that the KaMC derived from the KaMB, which is separated from the keratinocyte culture, has better proliferation capacity than a primary melanocyte. This indicates that the melanocyte, which is separated after being adapted to in vitro condition under keratinocyte environment, has much better proliferation capacity than the primary melanocyte directly separated from the skin tissue.

INDUSTRIAL APPLICABILITY

From one aspect, the present disclosure may provide a melanocyte or a melanoblast adapted in vitro while keeping the relation with a keratinocyte.

From one aspect, the present disclosure may make sure feasibility of studies of a melanocyte or a melanoblast conducted in vitro.

From one aspect of the present disclosure, risk factors and treatment methods of skin hyperpigmentation such as nevi, lentigo and age spot, achromatosis such as vitiligo (leukoplakia and albinism) or canities, or cancer such as melanoma may be found through studies of survival, propagation, differentiation and regeneration of a melanocyte or a melanoblast.

From one aspect, the present disclosure may facilitate the development of whitening cosmetics and medicines, which have purposes on reducing melisma and freckles, and inhibiting melanin pigment formation.

We claim:

1. A method for obtaining a keratinocyte-adapted melanocyte (KaMC) or melanoblast (KaMB), the method comprising:
   (a) culturing cells comprising keratinocytes in the absence of primary melanocytes in a keratinocyte medium in a dish, wherein the keratinocyte medium comprises human epidermal growth factor (hEGF), hydrocortisone, and epinephrine, and wherein the keratinocytes attach to the dish and proliferate in the medium;
   (b) removing the keratinocytes from the dish; and
   (c) culturing cells that remain attached to the dish in a melanocyte medium or a melanoblast medium to obtain the KaMC or KaMB.

2. The method of claim 1, wherein the melanocyte medium is a basal medium supplemented with supplements,
wherein the basal medium comprises essential and non-essential amino acids, vitamins, organic compounds, trace minerals and inorganic salts, but does not comprise antibiotics, antimycotics, hormones, growth factors or proteins,
wherein the supplements comprise fetal bovine serum, basic fibroblast growth factor, bovine pituitary extract, heparin, hydrocortisone, insulin, transferrin and phorbol 12-myristate 13-acetate (PMA).

3. The method of claim 1, wherein the melanoblast medium is a basal medium supplemented with supplements,
wherein the basal medium comprises essential and non-essential amino acids, vitamins, organic compounds, trace minerals and inorganic salts, but de does not comprise antibiotics, antimycotics, hormones, growth factors or proteins,
wherein the supplements comprise fetal bovine serum, basic fibroblast growth factor, bovine pituitary extract, heparin, hydrocortisone, insulin, transferrin and endothelin-1.

4. The method of claim 1, wherein the keratinocytes are human keratinocytes.

5. The method of claim 1 further comprising culturing the keratinocytes in a calcium medium prior to step (b).

6. The method of claim 1 further comprising:
(i) culturing the keratinocytes of step (a) in a calcium medium prior to step (b), wherein the calcium medium is a medium in which calcium is added to the keratinocyte medium and has a calcium concentration of 1.0 to 1.6 mM;
(ii) removing the calcium medium, washing the cells, exchanging the medium with a fresh keratinocyte medium and culturing the cells again;
(iii) removing the medium that was used for culturing the cells again in step (ii), washing the cells and incubating the cells; and
(iv) separating the keratinocytes in a sheet form from the incubated cells.

7. The method of claim 6, wherein the step (iv) comprises separating the keratinocytes in a sheet form by adding a buffer or a keratinocyte medium to the incubated cells.

8. The method of claim 6, wherein the step (i) is culturing the keratinocytes in a calcium medium, in which calcium is added to a keratinocyte medium, for 2 to 6 days.

9. The method of claim 6, which comprises exchanging the keratinocyte medium to a calcium medium at the time point when the keratinocytes are cultured in a culture dish at 80 to 100% confluency as the result of culturing the keratinocytes in a keratinocyte medium in the step (a).

10. The method of claim 6, wherein in the step (ii), the cells are cultured in the keratinocyte medium for 3 to 7 days.

11. The method of claim 6, wherein in the step (iii), the medium is removed at the time point when the color of the medium is not changed any more.

12. The method of claim 6, wherein in the step (iii), the incubation is conducted for 5 to 10 min.

13. A method for obtaining a keratinocyte-adapted melanocyte (KaMC) or keratinocyte-adapted melanoblast (KaMB), the method comprising:
(a) culturing cells comprising keratinocytes in a keratinocyte medium in a dish, wherein the keratinocyte medium comprises human epidermal growth factor (hEGF), hydrocortisone, and epinephrine, and wherein the keratinocytes attach to the dish and proliferate in the medium;
(b) removing the keratinocytes from the dish; and
(c) culturing cells that remain attached to the dish in a melanocyte medium or a melanoblast medium to obtain the KaMC or KaMB,
wherein the KaMC has at least one characteristic selected from:
(i) an expression level of p75NTR, which is a neural crest stem cell marker, is lower than a primary melanocyte;
(ii) an expression level of BRN2, which is expressed in a melanoblast, is higher than a primary melanocyte;
(iii) a melanin content that is higher than a primary melanocyte;
(iv) a tyrosinase activity that is higher than a primary melanocyte;
(v) an increased expression level of p75NTR that is higher than a primary melanocyte when cultured in a phorbol 12-myristate 13-acetate (PMA)-free medium;
(vi) an increased expression level of BRN2 that is lower than a primary melanocyte when cultured in a PMA-free medium;
(vii) a relative ratio of a p75NTR expression level of the melanocyte adapted to a keratinocyte cultured in a PMA-free medium, to the p75NTR expression level of the melanocyte adapted to a keratinocyte cultured in a PMA-containing melanocyte medium, is 60 to 160% of the ratio of the p75NTR expression level of a primary melanocyte cultured in a PMA-containing melanocyte medium, to the p75NTR expression level of the melanocyte adapted to a keratinocyte cultured in a PMA-containing melanocyte medium;
(viii) a relative ratio of a BRN2 expression level of the melanocyte adapted to a keratinocyte cultured in a PMA-free medium, to the BRN2 expression level of the melanocyte adapted to a keratinocyte cultured in a PMA-containing melanocyte medium, is 1 to 10 times the ratio of the BRN2 expression level of the melanocyte adapted to a keratinocyte cultured in a PMA-containing melanocyte medium, to the BRN2 expression level of the primary melanocyte cultured in a PMA-containing melanocyte medium; and
(ix) a ratio of the cells attached to the bottom of a dish to the total cultured cells after 2 hour subculture is higher than a primary melanocyte,
or the KaMB has at least one characteristic selected from:
(i) the expression level of at least one melanoblast marker selected from MITF, DCT, TYRP1, SNAI2, C-KIT, and EDNRB is higher than a primary melanocyte or a melanocyte adapted to a keratinocyte,
(ii) the expression level of at least one melanoblast marker selected from MITF and DCT is 2 times or higher than a primary melanocyte or a melanocyte adapted to a keratinocyte;
(iii) a BRN2 protein expression level is higher than a melanocyte adapted to a keratinocyte; and
(iv) a TYR protein expression level is lower than a melanocyte adapted to a keratinocyte.

* * * * *